US012564705B2

(12) United States Patent
Howell et al.

(10) Patent No.: US 12,564,705 B2
(45) Date of Patent: Mar. 3, 2026

(54) SPLITABLE NEEDLE AND DILATOR CATHETER PLACEMENT DEVICE AND ASSOCIATED METHODS

(71) Applicant: Bard Access Systems, Inc., Salt Lake City, UT (US)

(72) Inventors: Glade H. Howell, Draper, UT (US); Kyle G. Thornley, Farmington, UT (US); Zachary S. Hastings, Sterling, MD (US); Kent Diasabeygunawardena, Nashua, NH (US); Jon B. Taylor, Groton, MA (US); Taylor C. Tobin, Nashua, NH (US); Jacquelyn N. Phelps, Cambridge, MA (US); Daniel Hamilton, Mount Vernon, MA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 30 days.

(21) Appl. No.: 17/392,061

(22) Filed: Aug. 2, 2021

(65) Prior Publication Data

US 2022/0032014 A1    Feb. 3, 2022

Related U.S. Application Data

(60) Provisional application No. 63/060,639, filed on Aug. 3, 2020.

(51) Int. Cl.
*A61M 25/06*        (2006.01)
*A61M 25/00*        (2006.01)

(52) U.S. Cl.
CPC .... *A61M 25/0668* (2013.01); *A61M 25/0097* (2013.01); *A61M 25/0631* (2013.01); *A61M 2025/0675* (2013.01); *A61M 2205/02* (2013.01)

(58) Field of Classification Search
CPC ........ A61M 5/3278; A61M 2005/3284; A61M 5/321; A61M 25/0631; A61M 2025/0675;
(Continued)

(56) References Cited

U.S. PATENT DOCUMENTS 1,013,691  A    1/1912  Shields
3,225,762  A    12/1965  Guttman
(Continued)

FOREIGN PATENT DOCUMENTS

DE    202012006191 U1    7/2012
EP       0653220 A1     5/1995
(Continued)

OTHER PUBLICATIONS

PCT/US2021/028018 filed Apr. 19, 2021 International Preliminary Report on Patentability dated Jun. 3, 2022.
(Continued)

*Primary Examiner* — Michael J Tsai
*Assistant Examiner* — Kathleen Paige Farrell
(74) *Attorney, Agent, or Firm* — Rutan & Tucker LLP

(57) ABSTRACT

Disclosed herein is a catheter placement system including a splittable needle and dilator. The system can include a housing having one or more flexible sections and a pleated section. A user can grasp an elongate medical device using the flexible sections and transition the housing pleated section between an extended and collapsed configuration to urge the elongate medical device proximally or distally. The system can also include a needle retraction mechanism configured to split the needle long a longitudinal axis and roll up the separate portions to allow one or more elongate medical devices to pass therebetween. The system can also include a dilator splitter configured to separate a dilator along a longitudinal axis and radially displace the dilator portions to allow one or more elongate medical devices to
(Continued)

pass therebetween. Advantageously, the system can maintain the elongate medical device in a sterile environment, mitigating the introduction of pathogens.

15 Claims, 11 Drawing Sheets

(58) Field of Classification Search
CPC ...... A61M 2205/02; A61M 2005/3212; A61M 5/50; A61M 5/5086; A61M 25/0693; A61M 25/0097; A61M 25/0606; A61M 25/065; A61M 25/09041; A61M 25/09; A61M 2025/0681; A61M 25/0637; A61M 25/06; A61M 25/0662; A61M 25/01; A61M 25/0612; A61M 25/0668; A61M 25/0618; A61M 2039/087; A61M 39/08; A61B 17/3415
See application file for complete search history.

(56) References Cited

U.S. PATENT DOCUMENTS

| | | | |
|---|---|---|---|
| 3,325,061 A | 6/1967 | Ellsworth | |
| 3,382,872 A | 5/1968 | Rubin | |
| 3,570,485 A | 3/1971 | Reilly | |
| 3,890,976 A | 6/1975 | Bazell et al. | |
| 3,991,762 A * | 11/1976 | Radford | A61M 25/0111 |
| 4,205,675 A | 6/1980 | Vaillancourt | |
| 4,292,970 A | 10/1981 | Hession, Jr. | |
| 4,468,224 A | 8/1984 | Enzmann et al. | |
| 4,484,915 A | 11/1984 | Tartaglia | |
| 4,525,157 A | 6/1985 | Vaillancourt | |
| 4,581,019 A | 4/1986 | Curelaru et al. | |
| 4,594,073 A | 6/1986 | Stine | |
| 4,702,735 A | 10/1987 | Luther et al. | |
| 4,743,265 A | 5/1988 | Whitehouse et al. | |
| 4,766,908 A | 8/1988 | Clement | |
| 4,863,432 A | 9/1989 | Kvalo | |
| 4,935,008 A | 6/1990 | Lewis, Jr. | |
| 4,950,252 A * | 8/1990 | Luther | A61M 25/0631 |
| 4,957,489 A * | 9/1990 | Cameron et al. | A61M 25/0631 |
| 4,994,040 A | 2/1991 | Cameron et al. | |
| 5,017,259 A | 5/1991 | Kohsai | |
| 5,040,548 A | 8/1991 | Yock | |
| 5,057,073 A | 10/1991 | Martin | |
| 5,112,312 A | 5/1992 | Luther | |
| 5,115,816 A | 5/1992 | Lee | |
| 5,120,317 A | 6/1992 | Luther | |
| 5,158,544 A | 10/1992 | Weinstein | |
| 5,167,634 A * | 12/1992 | Corrigan, Jr. et al. | A61M 25/0668 |
| 5,188,593 A | 2/1993 | Martin | |
| 5,195,962 A | 3/1993 | Martin et al. | |
| 5,207,650 A | 5/1993 | Martin | |
| RE34,416 E | 10/1993 | Lemieux | |
| 5,267,958 A | 12/1993 | Buchbinder et al. | |
| 5,295,970 A | 3/1994 | Clinton et al. | |
| 5,306,247 A | 4/1994 | Pfenninger | |
| 5,312,361 A | 5/1994 | Zadini et al. | |
| 5,322,512 A | 6/1994 | Mohiuddin | |
| 5,328,472 A | 7/1994 | Steinke et al. | |
| 5,350,358 A | 9/1994 | Martin | |
| 5,358,495 A | 10/1994 | Lynn | |
| 5,364,355 A | 11/1994 | Alden et al. | |
| 5,368,567 A | 11/1994 | Lee | |
| 5,378,230 A | 1/1995 | Mahurkar | |
| 5,380,290 A | 1/1995 | Makower et al. | |
| 5,389,087 A | 2/1995 | Miraki | |
| 5,439,449 A | 8/1995 | Mapes et al. | |
| 5,443,457 A | 8/1995 | Ginn et al. | |
| 5,460,185 A | 10/1995 | Johnson et al. | |
| 5,489,271 A | 2/1996 | Andersen | |
| 5,573,520 A | 11/1996 | Schwartz et al. | |
| 5,584,813 A * | 12/1996 | Livingston et al. | A61M 25/0637 |

| | | | |
|---|---|---|---|
| 5,683,370 A | 11/1997 | Luther et al. | |
| 5,713,876 A | 2/1998 | Bogert et al. | |
| 5,718,678 A | 2/1998 | Fleming, III | |
| 5,772,636 A | 6/1998 | Brimhall et al. | |
| 5,885,251 A | 3/1999 | Luther | |
| 5,919,164 A | 7/1999 | Andersen | |
| 5,921,971 A | 7/1999 | Agro et al. | |
| 5,947,940 A | 9/1999 | Beisel | |
| 5,951,518 A * | 9/1999 | Licata et al. | A61M 25/0668 |
| 5,957,893 A | 9/1999 | Luther et al. | |
| 5,971,957 A * | 10/1999 | Luther et al. | A61M 25/065 |
| 6,159,198 A | 12/2000 | Gardeski et al. | |
| 6,197,007 B1 * | 3/2001 | Thorne et al. | A61M 25/0631 |
| 6,206,849 B1 | 3/2001 | Martin et al. | |
| 6,228,062 B1 | 5/2001 | Howell et al. | |
| 6,273,874 B1 * | 8/2001 | Parris | A61M 25/0631 |
| 6,475,187 B1 | 11/2002 | Gerberding | |
| 6,533,782 B2 | 3/2003 | Howell et al. | |
| 6,551,284 B1 | 4/2003 | Greenberg et al. | |
| 6,606,515 B1 | 8/2003 | Windheuser et al. | |
| 6,616,630 B1 | 9/2003 | Woehr et al. | |
| 6,626,869 B1 | 9/2003 | Bint | |
| 6,638,252 B2 | 10/2003 | Moulton et al. | |
| 6,716,228 B2 | 4/2004 | Tal | |
| 6,726,659 B1 | 4/2004 | Stocking et al. | |
| 6,819,951 B2 | 11/2004 | Patel et al. | |
| 6,821,287 B1 | 11/2004 | Jang | |
| 6,926,692 B2 | 8/2005 | Katoh et al. | |
| 6,962,575 B2 | 11/2005 | Tal | |
| 6,991,625 B1 | 1/2006 | Gately et al. | |
| 6,994,693 B2 | 2/2006 | Tal | |
| 6,999,809 B2 | 2/2006 | Currier et al. | |
| 7,025,746 B2 | 4/2006 | Tal | |
| 7,029,467 B2 | 4/2006 | Currier et al. | |
| 7,037,293 B2 | 5/2006 | Carrillo et al. | |
| 7,074,231 B2 | 7/2006 | Jang | |
| 7,094,222 B1 | 8/2006 | Siekas et al. | |
| 7,141,050 B2 | 11/2006 | Deal et al. | |
| 7,144,386 B2 | 12/2006 | Korkor et al. | |
| 7,311,697 B2 | 12/2007 | Osborne | |
| 7,364,566 B2 | 4/2008 | Elkins et al. | |
| 7,377,910 B2 | 5/2008 | Katoh et al. | |
| 7,390,323 B2 | 6/2008 | Jang | |
| D600,793 S | 9/2009 | Bierman et al. | |
| D601,242 S | 9/2009 | Bierman et al. | |
| D601,243 S | 9/2009 | Bierman et al. | |
| 7,594,911 B2 | 9/2009 | Powers et al. | |
| 7,691,093 B2 | 4/2010 | Brimhall | |
| 7,722,567 B2 | 5/2010 | Tal | |
| D617,893 S | 6/2010 | Bierman et al. | |
| D624,643 S | 9/2010 | Bierman et al. | |
| 7,819,889 B2 | 10/2010 | Healy et al. | |
| 7,857,788 B2 | 12/2010 | Racz | |
| D630,729 S | 1/2011 | Bierman et al. | |
| 7,909,797 B2 | 3/2011 | Kennedy, II et al. | |
| 7,909,811 B2 | 3/2011 | Agro et al. | |
| 7,922,696 B2 | 4/2011 | Tal et al. | |
| 7,938,820 B2 | 5/2011 | Webster et al. | |
| 7,967,834 B2 | 6/2011 | Tal et al. | |
| 7,976,511 B2 | 7/2011 | Fojtik | |
| 7,985,204 B2 | 7/2011 | Katoh et al. | |
| 8,073,517 B1 | 12/2011 | Burchman | |
| 8,105,286 B2 | 1/2012 | Anderson et al. | |
| 8,192,402 B2 | 6/2012 | Anderson et al. | |
| 8,202,251 B2 | 6/2012 | Bierman et al. | |
| 8,206,356 B2 | 6/2012 | Katoh et al. | |
| 8,361,011 B2 | 1/2013 | Mendels | |
| 8,372,107 B2 | 2/2013 | Tupper | |
| 8,377,006 B2 | 2/2013 | Tal et al. | |
| 8,454,577 B2 | 6/2013 | Joergensen et al. | |
| 8,585,858 B2 | 11/2013 | Kronfeld et al. | |
| 8,657,790 B2 | 2/2014 | Tal et al. | |
| 8,672,888 B2 | 3/2014 | Tal | |
| 8,696,645 B2 | 4/2014 | Tal et al. | |
| 8,784,362 B2 | 7/2014 | Boutilette et al. | |
| 8,827,958 B2 | 9/2014 | Bierman et al. | |
| 8,876,704 B2 | 11/2014 | Golden et al. | |
| 8,882,713 B1 | 11/2014 | Call et al. | |
| 8,900,192 B2 | 12/2014 | Anderson et al. | |

(56) References Cited

U.S. PATENT DOCUMENTS

| | | | |
|---|---|---|---|
| 8,900,207 B2 | 12/2014 | Uretsky | |
| 8,915,884 B2 | 12/2014 | Tal et al. | |
| 8,956,327 B2 | 2/2015 | Bierman et al. | |
| 9,023,093 B2 | 5/2015 | Pal | |
| 9,067,023 B2 | 6/2015 | Bertocci | |
| 9,126,012 B2 | 9/2015 | McKinnon et al. | |
| 9,138,252 B2 | 9/2015 | Bierman et al. | |
| 9,180,275 B2 | 11/2015 | Helm | |
| 9,265,920 B2 | 2/2016 | Rundquist et al. | |
| 9,272,121 B2 | 3/2016 | Piccagli | |
| 9,445,734 B2 | 9/2016 | Grunwald | |
| 9,522,254 B2 | 12/2016 | Belson | |
| 9,554,785 B2 | 1/2017 | Walters et al. | |
| 9,566,087 B2 | 2/2017 | Bierman et al. | |
| 9,675,784 B2 | 6/2017 | Belson | |
| 9,713,695 B2 | 7/2017 | Bunch et al. | |
| 9,764,117 B2 | 9/2017 | Bierman et al. | |
| 9,770,573 B2 | 9/2017 | Golden et al. | |
| 9,814,861 B2 | 11/2017 | Boutillette et al. | |
| 9,820,845 B2 | 11/2017 | von Lehe et al. | |
| 9,861,383 B2 | 1/2018 | Clark | |
| 9,872,971 B2* | 1/2018 | Blanchard | A61M 25/09041 |
| 9,884,169 B2 | 2/2018 | Bierman et al. | |
| 9,889,275 B2 | 2/2018 | Voss et al. | |
| 9,913,585 B2 | 3/2018 | McCaffrey et al. | |
| 9,913,962 B2 | 3/2018 | Tal et al. | |
| 9,981,113 B2 | 5/2018 | Bierman | |
| 10,010,312 B2 | 7/2018 | Tegels | |
| 10,065,020 B2 | 9/2018 | Gaur | |
| 10,086,170 B2 | 10/2018 | Chhikara et al. | |
| 10,098,724 B2 | 10/2018 | Adams et al. | |
| 10,111,683 B2 | 10/2018 | Tsamir et al. | |
| 10,118,020 B2 | 11/2018 | Avneri et al. | |
| 10,130,269 B2 | 11/2018 | McCaffrey et al. | |
| 10,220,184 B2 | 3/2019 | Clark | |
| 10,220,191 B2 | 3/2019 | Belson et al. | |
| 10,265,508 B2 | 4/2019 | Baid | |
| 10,271,873 B2 | 4/2019 | Steingisser et al. | |
| 10,376,675 B2 | 8/2019 | Mitchell et al. | |
| 10,675,440 B2 | 6/2020 | Abitabilo et al. | |
| 10,688,281 B2 | 6/2020 | Blanchard et al. | |
| 10,806,901 B2 | 10/2020 | Burkholz et al. | |
| 10,926,060 B2* | 2/2021 | Stern et al. | A61M 25/0068 |
| 11,260,206 B2 | 3/2022 | Stone et al. | |
| 11,400,260 B2 | 8/2022 | Huang et al. | |
| 11,759,607 B1 | 9/2023 | Biancarelli | |
| 2002/0040231 A1 | 4/2002 | Wysoki | |
| 2002/0045843 A1* | 4/2002 | Barker et al. | A61M 25/0631 |
| 2002/0198492 A1 | 12/2002 | Miller et al. | |
| 2003/0036712 A1 | 2/2003 | Heh et al. | |
| 2003/0060863 A1 | 3/2003 | Dobak | |
| 2003/0088212 A1 | 5/2003 | Tal | |
| 2003/0100849 A1 | 5/2003 | Jang | |
| 2003/0153874 A1 | 8/2003 | Tal | |
| 2003/0158514 A1 | 8/2003 | Tal | |
| 2004/0015138 A1 | 1/2004 | Currier et al. | |
| 2004/0049157 A1 | 3/2004 | Plishka et al. | |
| 2004/0064086 A1 | 4/2004 | Gottlieb et al. | |
| 2004/0092879 A1 | 5/2004 | Kraus et al. | |
| 2004/0116864 A1 | 6/2004 | Boudreaux | |
| 2004/0116901 A1 | 6/2004 | Appling | |
| 2004/0167478 A1 | 8/2004 | Mooney et al. | |
| 2004/0193093 A1 | 9/2004 | Desmond | |
| 2004/0230178 A1 | 11/2004 | Wu | |
| 2005/0004554 A1 | 1/2005 | Osborne | |
| 2005/0120523 A1 | 6/2005 | Schweikert | |
| 2005/0131343 A1 | 6/2005 | Abrams et al. | |
| 2005/0148936 A1 | 7/2005 | Moss | |
| 2005/0215956 A1 | 9/2005 | Nerney | |
| 2005/0215958 A1 | 9/2005 | Hawthorne | |
| 2005/0245882 A1 | 11/2005 | Elkins et al. | |
| 2005/0283221 A1 | 12/2005 | Mann et al. | |
| 2006/0009740 A1 | 1/2006 | Higgins et al. | |
| 2006/0116629 A1 | 6/2006 | Tal et al. | |
| 2006/0129100 A1 | 6/2006 | Tal | |
| 2006/0129130 A1 | 6/2006 | Tal et al. | |
| 2007/0276288 A1 | 11/2007 | Khaw | |
| 2008/0045894 A1 | 2/2008 | Perchik et al. | |
| 2008/0091137 A1 | 4/2008 | Reavill | |
| 2008/0125744 A1 | 5/2008 | Treacy | |
| 2008/0125748 A1 | 5/2008 | Patel | |
| 2008/0132850 A1 | 6/2008 | Fumiyama et al. | |
| 2008/0262430 A1 | 10/2008 | Anderson et al. | |
| 2008/0262431 A1 | 10/2008 | Anderson et al. | |
| 2008/0294111 A1 | 11/2008 | Tal et al. | |
| 2008/0312578 A1 | 12/2008 | DeFonzo et al. | |
| 2008/0319387 A1* | 12/2008 | Amisar et al. | A61M 25/0606 |
| 2009/0131872 A1 | 5/2009 | Popov | |
| 2009/0187147 A1 | 7/2009 | Kurth et al. | |
| 2009/0221961 A1 | 9/2009 | Tal et al. | |
| 2009/0270889 A1 | 10/2009 | Tal et al. | |
| 2009/0292272 A1* | 11/2009 | McKinnon | A61M 25/0668 |
| 2010/0030154 A1 | 2/2010 | Duffy | |
| 2010/0256487 A1 | 10/2010 | Hawkins et al. | |
| 2010/0298839 A1* | 11/2010 | Castro | A61B 17/3421 |
| 2010/0305474 A1 | 12/2010 | DeMars et al. | |
| 2011/0004162 A1 | 1/2011 | Tal | |
| 2011/0009827 A1 | 1/2011 | Bierman et al. | |
| 2011/0021994 A1 | 1/2011 | Anderson et al. | |
| 2011/0066142 A1 | 3/2011 | Tal et al. | |
| 2011/0071502 A1 | 3/2011 | Asai | |
| 2011/0144620 A1 | 6/2011 | Tal | |
| 2011/0152836 A1 | 6/2011 | Riopelle et al. | |
| 2011/0190778 A1 | 8/2011 | Arpasi et al. | |
| 2011/0202006 A1 | 8/2011 | Bierman et al. | |
| 2011/0230844 A1 | 9/2011 | Shaw et al. | |
| 2011/0251559 A1 | 10/2011 | Tal et al. | |
| 2011/0270192 A1 | 11/2011 | Anderson et al. | |
| 2012/0016346 A1 | 1/2012 | Steinmetz et al. | |
| 2012/0041371 A1 | 2/2012 | Tal et al. | |
| 2012/0065590 A1 | 3/2012 | Bierman et al. | |
| 2012/0078231 A1 | 3/2012 | Hoshinouchi | |
| 2012/0130411 A1 | 5/2012 | Tal et al. | |
| 2012/0130415 A1 | 5/2012 | Tal et al. | |
| 2012/0157854 A1 | 6/2012 | Kurrus et al. | |
| 2012/0215171 A1* | 8/2012 | Christiansen | A61M 25/0668 |
| 2012/0220942 A1 | 8/2012 | Hall et al. | |
| 2012/0226239 A1* | 9/2012 | Green | A61M 5/1782 |
| 2012/0283640 A1 | 11/2012 | Anderson et al. | |
| 2012/0316500 A1 | 12/2012 | Bierman et al. | |
| 2013/0053763 A1 | 2/2013 | Makino et al. | |
| 2013/0053826 A1 | 2/2013 | Shevgoor | |
| 2013/0123704 A1 | 5/2013 | Bierman et al. | |
| 2013/0158338 A1 | 6/2013 | Kelly et al. | |
| 2013/0158506 A1 | 6/2013 | Harris et al. | |
| 2013/0188291 A1 | 7/2013 | Vardiman | |
| 2013/0237931 A1 | 9/2013 | Tal et al. | |
| 2013/0306079 A1 | 11/2013 | Tracy | |
| 2014/0025036 A1 | 1/2014 | Bierman et al. | |
| 2014/0081210 A1 | 3/2014 | Bierman et al. | |
| 2014/0094774 A1 | 4/2014 | Blanchard | |
| 2014/0100552 A1 | 4/2014 | Gallacher et al. | |
| 2014/0171833 A1 | 6/2014 | Matsuno et al. | |
| 2014/0207052 A1 | 7/2014 | Tal et al. | |
| 2014/0207069 A1 | 7/2014 | Bierman et al. | |
| 2014/0214005 A1 | 7/2014 | Belson | |
| 2014/0257111 A1 | 9/2014 | Yamashita et al. | |
| 2014/0276432 A1 | 9/2014 | Bierman et al. | |
| 2014/0276599 A1 | 9/2014 | Cully et al. | |
| 2015/0011834 A1 | 1/2015 | Ayala et al. | |
| 2015/0080939 A1 | 3/2015 | Adams et al. | |
| 2015/0094653 A1 | 4/2015 | Pacheco et al. | |
| 2015/0112307 A1 | 4/2015 | Margolis | |
| 2015/0112310 A1 | 4/2015 | Call et al. | |
| 2015/0119806 A1 | 4/2015 | Blanchard et al. | |
| 2015/0126930 A1 | 5/2015 | Bierman et al. | |
| 2015/0148595 A1 | 5/2015 | Bagwell et al. | |
| 2015/0157829 A1 | 6/2015 | Bunch et al. | |
| 2015/0190168 A1 | 7/2015 | Bierman et al. | |
| 2015/0196210 A1 | 7/2015 | McCaffrey et al. | |
| 2015/0224287 A1 | 8/2015 | Bian et al. | |
| 2015/0231364 A1 | 8/2015 | Blanchard et al. | |
| 2015/0283357 A1 | 10/2015 | Lampropoulos et al. | |
| 2015/0290431 A1 | 10/2015 | Hall et al. | |

(56) References Cited

U.S. PATENT DOCUMENTS

| | | |
|---|---|---|
| 2015/0297868 A1 | 10/2015 | Tal et al. |
| 2015/0306356 A1 | 10/2015 | Gill |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0001046 A1 | 1/2016 | Tietze |
| 2016/0030716 A1 | 2/2016 | Mallin et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1 | 8/2016 | Mitchell et al. |
| 2016/0220811 A1 | 8/2016 | Spotnitz et al. |
| 2016/0242661 A1 | 8/2016 | Fischell et al. |
| 2016/0256101 A1 | 9/2016 | Aharoni et al. |
| 2016/0325073 A1 | 11/2016 | Davies et al. |
| 2016/0331938 A1 | 11/2016 | Blanchard et al. |
| 2016/0338728 A1 | 11/2016 | Tal |
| 2016/0346503 A1 | 12/2016 | Jackson et al. |
| 2017/0028135 A1 | 2/2017 | Fransson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |
| 2017/0182293 A1 | 6/2017 | Chhikara et al. |
| 2017/0239443 A1 | 8/2017 | Abitabilo et al. |
| 2017/0259043 A1 | 9/2017 | Chan et al. |
| 2017/0273713 A1 | 9/2017 | Shah et al. |
| 2017/0274182 A1 | 9/2017 | O'Bryan et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0001062 A1* | 1/2018 | O'Carrol et al. . A61M 25/0668 |
| 2018/0008294 A1 | 1/2018 | Garrison et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0229004 A1 | 8/2018 | Blanchard et al. |
| 2018/0296799 A1 | 10/2018 | Horst et al. |
| 2018/0296804 A1 | 10/2018 | Bierman |
| 2018/0310955 A1* | 11/2018 | Lindekugel ............ A61B 90/96 |
| 2018/0369540 A1 | 12/2018 | Asai |
| 2019/0015646 A1 | 1/2019 | Matlock et al. |
| 2019/0021640 A1 | 1/2019 | Burkholz et al. |
| 2019/0038113 A1 | 2/2019 | Chu |
| 2019/0060616 A1 | 2/2019 | Solomon |
| 2019/0076167 A1 | 3/2019 | Fantuzzi et al. |
| 2019/0076628 A1* | 3/2019 | Anstett ............ A61M 25/0668 |
| 2019/0134349 A1 | 5/2019 | Cohn et al. |
| 2019/0192824 A1* | 6/2019 | Cordeiro et al. . A61M 25/0606 |
| 2019/0201665 A1 | 7/2019 | Turpin |
| 2019/0209812 A1 | 7/2019 | Burkholz et al. |
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2019/0351196 A1 | 11/2019 | Ribelin et al. |
| 2020/0001051 A1* | 1/2020 | Huang et al. ......... A61M 25/06 |
| 2020/0016374 A1 | 1/2020 | Burkholz et al. |
| 2020/0046948 A1* | 2/2020 | Burkholz et al. . A61M 25/0606 |
| 2020/0100716 A1 | 4/2020 | Devgon et al. |
| 2020/0129732 A1 | 4/2020 | Vogt et al. |
| 2020/0147349 A1 | 5/2020 | Holt |
| 2020/0197579 A1 | 6/2020 | Chu et al. |
| 2020/0197682 A1 | 6/2020 | Franklin et al. |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0060306 A1 | 3/2021 | Kumar |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1 | 4/2021 | DiCianni |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0244920 A1 | 8/2021 | Kujawa et al. |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001109 A1 | 1/2022 | Simon |
| 2022/0001138 A1 | 1/2022 | Howell |
| 2022/0032013 A1 | 2/2022 | Howell et al. |
| 2022/0062528 A1 | 3/2022 | Thornley et al. |
| 2022/0062596 A1 | 3/2022 | Ribelin et al. |
| 2022/0126064 A1 | 4/2022 | Tobin et al. |
| 2022/0193376 A1 | 6/2022 | Spataro et al. |
| 2022/0193377 A1 | 6/2022 | Haymond et al. |
| 2022/0193378 A1 | 6/2022 | Spataro et al. |
| 2022/0323723 A1 | 10/2022 | Spataro et al. |
| 2022/0331562 A1 | 10/2022 | Jaros et al. |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |
| 2023/0173231 A1 | 6/2023 | Parikh et al. |
| 2023/0233814 A1 | 7/2023 | Howell et al. |
| 2023/0381459 A1 | 11/2023 | Belson et al. |
| 2023/0381481 A1 | 11/2023 | Pizzato |
| 2024/0009427 A1 | 1/2024 | Howell et al. |
| 2024/0050706 A1 | 2/2024 | Howell et al. |
| 2024/0198058 A1 | 6/2024 | Howell et al. |
| 2025/0001136 A1 | 1/2025 | Mitchell et al. |
| 2025/0065083 A1 | 2/2025 | Haymond et al. |
| 2025/0082906 A1 | 3/2025 | Howell et al. |
| 2025/0222237 A1 | 7/2025 | Spataro et al. |
| 2025/0235669 A1 | 7/2025 | Howell |

FOREIGN PATENT DOCUMENTS

| | | | |
|---|---|---|---|
| EP | 0730880 A1 | 9/1996 | |
| EP | 2061385 A1 | 5/2009 | |
| EP | 2061385 B1 | 5/2009 | |
| EP | 1458437 B1 | 3/2010 | |
| EP | 2248549 A2 | 11/2010 | |
| EP | 2319576 A1 | 5/2011 | |
| EP | 2366422 A1 | 9/2011 | |
| EP | 2486880 A2 | 8/2012 | |
| EP | 2486881 A2 | 8/2012 | |
| EP | 2486951 A2 | 8/2012 | |
| EP | 2512576 A2 | 10/2012 | |
| EP | 2152348 B1 | 2/2015 | |
| EP | 2512576 B1 | 5/2016 | |
| EP | 3473291 A1 | 4/2019 | |
| EP | 3093038 B1 | 5/2019 | |
| EP | 2260897 B1 | 9/2019 | |
| EP | 3693051 A1 | 8/2020 | |
| GB | 1273547 A | 5/1972 | |
| JP | 2004248987 A | 9/2004 | |

(56)                References Cited

FOREIGN PATENT DOCUMENTS

| | | | |
|----|----------------|-----|---------|
| JP | 2008054859 A   |     | 3/2008  |
| WO | 94/21315 A1    |     | 9/1994  |
| WO | 95/32009 A2    |     | 11/1995 |
| WO | 98/44979 A1    |     | 10/1998 |
| WO | 98/53871 A1    |     | 12/1998 |
| WO | 9857685 A1     |     | 12/1998 |
| WO | 99/12600 A1    |     | 3/1999  |
| WO | 99/26681 A1    |     | 6/1999  |
| WO | 00/06221 A1    |     | 2/2000  |
| WO | 0054830 A1     |     | 9/2000  |
| WO | 2003008020 A1  |     | 1/2003  |
| WO | 2003057272 A2  |     | 7/2003  |
| WO | 03/068073 A1   |     | 8/2003  |
| WO | 2003066125 A2  |     | 8/2003  |
| WO | 2005096778 A2  |     | 10/2005 |
| WO | 2006055288 A2  |     | 5/2006  |
| WO | 2006055780 A2  |     | 5/2006  |
| WO | 2007046850 A2  |     | 4/2007  |
| WO | 2008033983 A1  |     | 3/2008  |
| WO | 2008092029 A2  |     | 7/2008  |
| WO | 2008/131300 A2 |     | 10/2008 |
| WO | 2008131289 A2  |     | 10/2008 |
| WO | 2009114833 A1  |     | 9/2009  |
| WO | 2009114837 A2  |     | 9/2009  |
| WO | 2010/048449 A2 |     | 4/2010  |
| WO | 2010056906 A2  |     | 5/2010  |
| WO | 2010083467 A2  |     | 7/2010  |
| WO | 2010/132608 A2 |     | 11/2010 |
| WO | 2011081859 A2  |     | 7/2011  |
| WO | 2011097639 A2  |     | 8/2011  |
| WO | 2011109792 A1  |     | 9/2011  |
| WO | 2011146764 A1  |     | 11/2011 |
| WO | 2012068162 A2  |     | 5/2012  |
| WO | 2012068166 A2  |     | 5/2012  |
| WO | 2012135761 A1  |     | 10/2012 |
| WO | 2012/154277 A1 |     | 11/2012 |
| WO | 2012162677 A1  |     | 11/2012 |
| WO | 2013026045 A1  |     | 2/2013  |
| WO | 2013138519 A1  |     | 9/2013  |
| WO | 2014006403 A1  |     | 1/2014  |
| WO | 2014/100392 A1 |     | 6/2014  |
| WO | 2014113257 A2  |     | 7/2014  |
| WO | 2014152005 A2  |     | 9/2014  |
| WO | 2014197614 A2  |     | 12/2014 |
| WO | 2015057766 A1  |     | 4/2015  |
| WO | 2015077560 A1  |     | 5/2015  |
| WO | 2015/168655 A2 |     | 11/2015 |
| WO | 2016110824 A1  |     | 7/2016  |
| WO | 2016123278 A1  |     | 8/2016  |
| WO | 2016139590 A1  |     | 9/2016  |
| WO | 2016139597 A2  |     | 9/2016  |
| WO | 2016/178974 A1 |     | 11/2016 |
| WO | 2016/187063 A1 |     | 11/2016 |
| WO | 2016176065 A1  |     | 11/2016 |
| WO | 2018089275 A1  |     | 5/2018  |
| WO | 2018089285 A1  |     | 5/2018  |
| WO | 2018089385 A1  |     | 5/2018  |
| WO | 2018191547 A1  |     | 10/2018 |
| WO | 2018213148 A1  |     | 11/2018 |
| WO | 2018218236 A1  |     | 11/2018 |
| WO | 2019/050576 A1 |     | 3/2019  |
| WO | 2019/146026 A1 |     | 8/2019  |
| WO | 2019199734 A1  |     | 10/2019 |
| WO | 2020014149 A1  |     | 1/2020  |
| WO | 2020069395 A1  |     | 4/2020  |
| WO | 2020/109448 A1 |     | 6/2020  |
| WO | 2020/113123 A1 |     | 6/2020  |
| WO | 2021038041 A1  |     | 3/2021  |
| WO | 2021050302 A1  |     | 3/2021  |
| WO | 2021/077103 A1 |     | 4/2021  |
| WO | 2021062023 A1  |     | 4/2021  |
| WO | 2021081205 A1  |     | 4/2021  |
| WO | 2021086793 A1  |     | 5/2021  |
| WO | 2021/236950 A1 |     | 11/2021 |
| WO | 2021226050 A1  |     | 11/2021 |
| WO | 2022031618 A1  |     | 2/2022  |
| WO | 2022/094141 A1 |     | 5/2022  |
| WO | 2022/133297 A1 |     | 6/2022  |
| WO | 2022-140406 A1 |     | 6/2022  |
| WO | 2022/140429 A1 |     | 6/2022  |
| WO | 2022/217098 A1 |     | 10/2022 |
| WO | 2023014994 A1  |     | 2/2023  |
| WO | 2023/049498 A1 |     | 3/2023  |
| WO | 2023049505 A1  |     | 3/2023  |
| WO | 2023049511 A1  |     | 3/2023  |
| WO | 2023049519 A1  |     | 3/2023  |
| WO | 2023049522 A1  |     | 3/2023  |
| WO | 2023146792 A1  |     | 8/2023  |

OTHER PUBLICATIONS

PCT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.
PCT/US2021/064671 filed Dec. 21, 2021 International Search Report and Written Opinion dated May 27, 2022.
PCT/US2022/024085 filed Apr. 8, 2022 International Search Report and Wirtten Opinion dated Sep. 12, 2022.
U.S. Appl. No. 16/398,020, filed Apr. 29, 2019 Examiner's Answer dated Oct. 31, 2022.
U.S. Appl. No. 17/031,478, filed Sep. 24, 2020 Notice of Allowance dated Sep. 16, 2022.
U.S. Appl. No. 17/156,252, filed Jan. 22, 2021 Non-Final Office Action dated Oct. 25, 2022.
PCT/US2020/052536 filed Sep. 24, 2020 International Search Report and Written Opinion dated Dec. 4, 2020.
PCT/US2021/014700 filed Jan. 22, 2021 International Search Report and Written Opinion dated Jun. 29, 2021.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/039084 filed Jun. 25, 2021 International Search Report and Written Opinion dated Jan. 10, 2022.
PCT/US2021/044029 filed Jul. 30, 2021 International Search Report and Written Opinion dated Dec. 9, 2021.
PCT/US2021/048275 filed Aug. 30, 2021 International Search Report and Written Opinion dated Jan. 4, 2022.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Final Office Action dated Jan. 25, 2022.
U.S. Appl. No. 16/398,020, filed Apr. 29, 2019 Non-Final Office Action dated May 11, 2021.
U.S. Appl. No. 17/031,478, filed Sep. 24, 2020 Non-Final Office Action dated May 11, 2022.
PCT/US2021/057135 filed Oct. 28, 2021 International Preliminary Report on Patentability dated May 2, 2023.
PCT/US2021/057135 filed Oct. 28, 2021 International Search Report and Written Opinion dated Mar. 11, 2022.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.

(56)                    References Cited

OTHER PUBLICATIONS

PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
PCT/US2021/044223 filed Aug. 2, 2021 International Search Report and Written Opinion dated Dec. 21, 2021.
U.S. Appl. No. 15/008,628, filed Jan. 28, 2016 Final Office Action dated May 30, 2018.
PCT/US2023/011173 filed Jan. 19, 2023 International Search Report and Written Opinion dated May 22, 2023.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/240,591, filed Apr. 26, 2021 Non-Final Office Action dated Jun. 8, 2023.
U.S. Appl. No. 17/326,017, filed May 20, 2021 Notice of Allowance dated Jul. 3, 2023.
U.S. Appl. No. 17/358,504, filed Jun. 25, 2021 Non-Final Office Action dated Oct. 4, 2023.
U.S. Appl. No. 17/358,504, filed Jun. 25, 2021 Restriction Requirement dated Jun. 7, 2023.
U.S. Appl. No. 17/360,694, filed Jun. 28, 2021 Restriction Requirement dated Jul. 20, 2023.
U.S. Appl. No. 17/390,682, filed Jul. 30, 2021 Final Office Action dated Jul. 27, 2023.
U.S. Appl. No. 17/513,789, filed Oct. 28, 2021 Restriction Requirement dated Oct. 3, 2023.
U.S. Appl. No. 16/398,020, filed Apr. 29, 2019 Board Decision dated Oct. 30, 2023.
U.S. Appl. No. 17/237,909, filed Apr. 22, 2021 Notice of Allowance dated Oct. 27, 2023.
U.S. Appl. No. 17/240,591, filed Apr. 26, 2021 Final Office Action dated Dec. 6, 2023.
U.S. Appl. No. 17/360,694, filed Jun. 28, 2021 Non-Final Office Action dated Oct. 13, 2023.
U.S. Appl. No. 17/390,682, filed Jul. 30, 2021 Non-Final Office Action dated Dec. 1, 2023.
U.S. Appl. No. 17/557,924, filed Dec. 21, 2021 Non-Final Office Action dated Nov. 3, 2023.
U.S. Appl. No. 16/398,020, filed Apr. 29, 2019 Non-Final Office Action dated Jan. 18, 2024.
U.S. Appl. No. 16/398,020, filed Apr. 29, 2019 Notice of Allowance dated May 20, 2024.
U.S. Appl. No. 17/234,611, filed Apr. 19, 2021 Non-Final Office Action dated Apr. 23, 2024.
U.S. Appl. No. 17/234,611, filed Apr. 19, 2021 Restriction Requirement dated Jan. 18, 2024.
U.S. Appl. No. 17/240,591, filed Apr. 26, 2021 Advisory Action dated Feb. 22, 2024.
U.S. Appl. No. 17/240,591, filed Apr. 26, 2021 Non-Final Office Action dated Jun. 4, 2024.
U.S. Appl. No. 17/358,504, filed Jun. 25, 2021 Final Office Action dated Mar. 13, 2024.
U.S. Appl. No. 17/358,504, filed Jun. 25, 2021 Notice of Allowance dated Jul. 17, 2024.
U.S. Appl. No. 17/360,694, filed Jun. 28, 2021 Non-Final Office Action dated Feb. 14, 2024.
U.S. Appl. No. 17/390,682, filed Jul. 30, 2021 Final Office Action dated May 6, 2024.
U.S. Appl. No. 17/390,682, filed Jul. 30, 2021 Non-Final Office Action dated Jul. 5, 2024.
U.S. Appl. No. 17/513,789, filed Oct. 28, 2021 Final Office Action dated Jul. 9, 2024.
U.S. Appl. No. 17/513,789, filed Oct. 28, 2021 Non-Final Office Action dated Jan. 9, 2024.
U.S. Appl. No. 17/554,978, filed Dec. 17, 2021 Non-Final Office Action dated Apr. 19, 2024.
U.S. Appl. No. 17/557,924, filed Dec. 21, 2021 Final Office Action dated Feb. 29, 2024.
U.S. Appl. No. 17/234,611, filed Apr. 19, 2021 Final Office Action dated Sep. 20, 2024.
U.S. Appl. No. 17/240,591, filed Apr. 26, 2021 Final Office Action dated Aug. 14, 2024.
U.S. Appl. No. 17/554,978, filed Dec. 17, 2021 Notice of Allowance dated Jul. 24, 2024.
U.S. Appl. No. 17/557,924, filed Dec. 21, 2021 Non-Final Office Action dated Aug. 20, 2024.
U.S. Appl. No. 17/558,124, filed Dec. 21, 2021 Non-Final Office Action dated Sep. 20, 2024.
U.S. Appl. No. 17/360,694, filed Jun. 28, 2021 Notice of Allowance dated Dec. 16, 2024.
U.S. Appl. No. 17/461,619, filed Aug. 30, 2021 Non-Final Office Action dated Feb. 11, 2025.
U.S. Appl. No. 17/461,619, filed Aug. 30, 2021 Restriction Requirement dated Dec. 6, 2024.
U.S. Appl. No. 17/513,789, filed Oct. 28, 2021 Notice of Allowance dated Jan. 3, 2025.
U.S. Appl. No. 17/557,924, filed Dec. 21, 2021 Notice of Allowance dated Dec. 11, 2024.
U.S. Appl. No. 17/234,611, filed Apr. 19, 2021 Examiner's Answer dated May 1, 2025.
U.S. Appl. No. 17/390,682, filed Jul. 30, 2021 Final Office Action dated Feb. 28, 2025.
U.S. Appl. No. 17/461,619, filed Aug. 30, 2021 Final Office Action dated Jun. 2, 2025.
U.S. Appl. No. 17/558,124. filed Dec. 21, 2021 Notice of Allowance dated Mar. 7, 2025.
U.S. Appl. No. 17/716,675, filed Apr. 8, 2022 Restriction Requirement dated Jul. 2, 2025.
U.S. Appl. No. 17/461,619 filed Aug. 30, 2021 Advisory Action dated Aug. 14, 2025.
U.S. Appl. No. 17/461,619 filed Aug. 30, 2021 Non-Final Office Action dated Oct. 7, 2025.
U.S. Appl. No. 17/716,675 filed Apr. 8, 2022 Non-Final Office Action dated Sep. 11, 2025.
U.S. Appl. No. 17/882,388 filed Aug. 5, 2022 Non-Final Office Action dated Aug. 20, 2025.
U.S. Appl. No. 17/953,663 filed Sep. 27, 2022 Restriction Requirement dated Oct. 3, 2025.
U.S. Appl. No. 17/953,860 filed Sep. 27, 2022 Restriction Requirement dated Oct. 22, 2025.
U.S. Appl. No. 17/953,959 filed Sep. 27, 2022 Restriction Requirement dated Oct. 22, 2025.
U.S. Appl. No. 17/954,096 filed Sep. 27, 2022 Non-Final Office Action dated Aug. 26, 2025.
U.S. Appl. No. 17/954,132 filed Sep. 27, 2022 Non-Final Office Action dated Aug. 21, 2025.

* cited by examiner 110
116
112
112
116
150
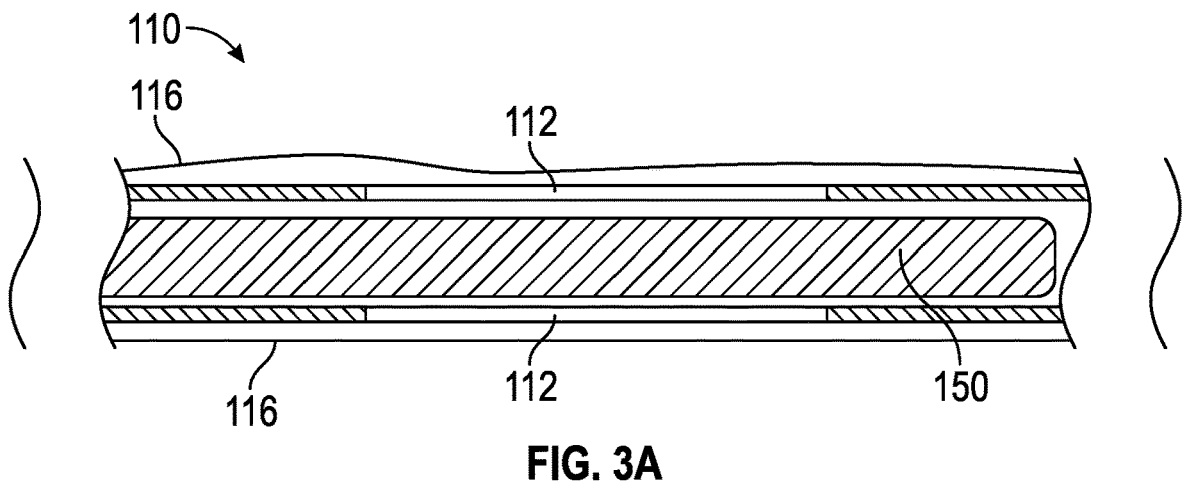
FIG. 3A
110
116
112
112
116
150
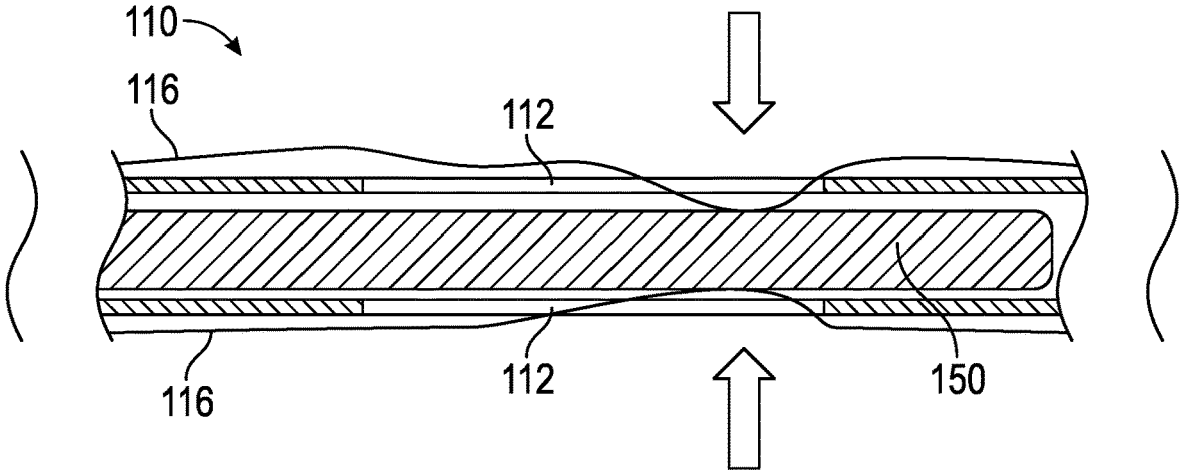
FIG. 3B
110
116
112
116
150
112
FIG. 3C

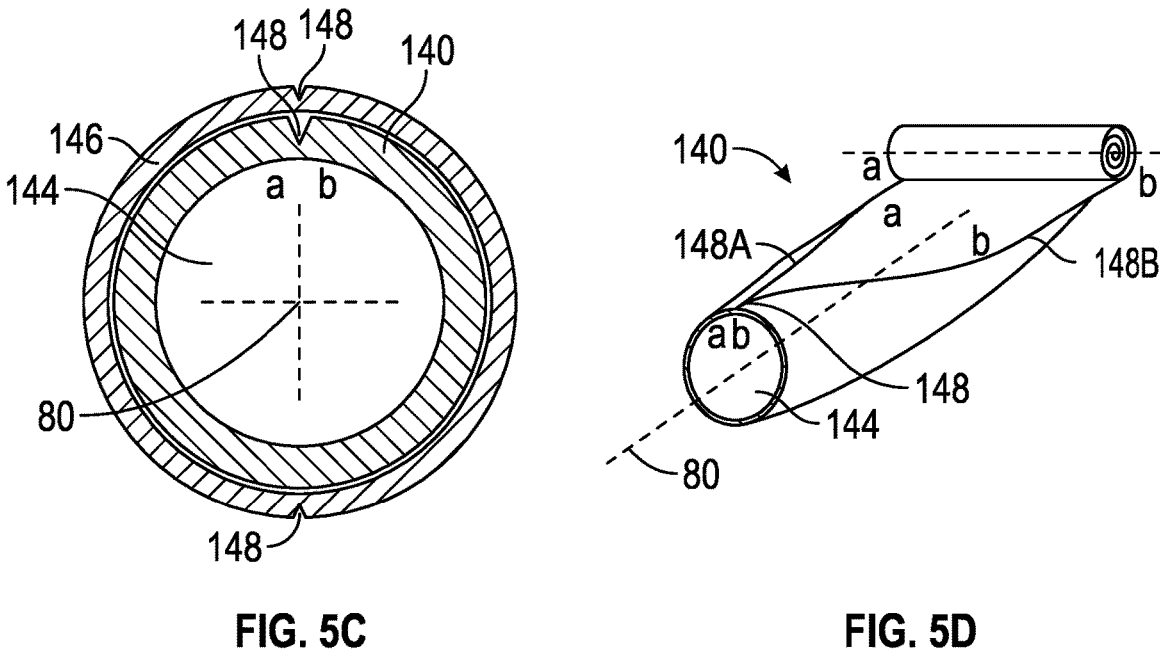
FIG. 5C                    FIG. 5D
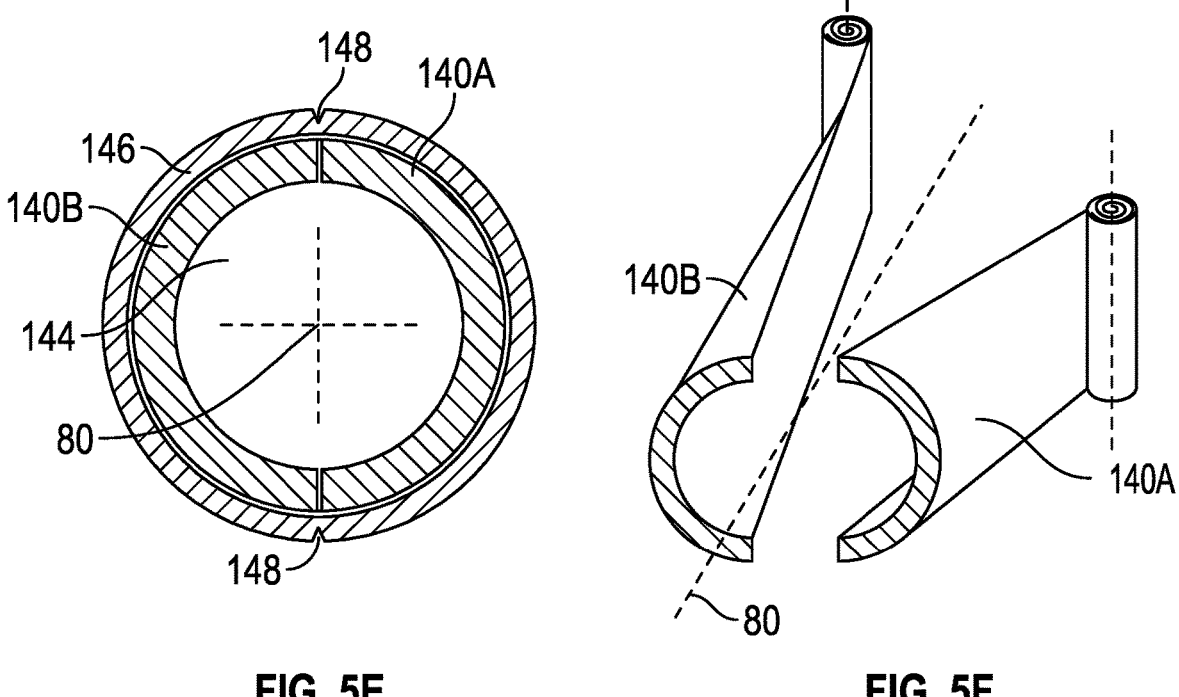
FIG. 5E                    FIG. 5F

SPLITABLE NEEDLE AND DILATOR CATHETER PLACEMENT DEVICE AND ASSOCIATED METHODS

PRIORITY

This application claims the benefit of priority to U.S. Patent Application No. 63/060,639, filed Aug. 3, 2020, which is incorporated by reference in its entirety into this application.

SUMMARY

Embodiments disclosed herein are directed to catheter placement systems including a splittable needle and a splittable dilator. The system includes a housing having one or more flexible sections and a pleated section. A user can grasp an elongate medical device using the flexible sections and transition the housing pleated section between an extended and a collapsed configuration to urge the elongate medical device proximally or distally. Further, the housing includes a needle retraction mechanism configured to split the needle along a longitudinal axis and roll up the separate portions to allow one or more elongate medical devices to pass therebetween. The system also includes a dilator splitter configured to separate a dilator along a longitudinal axis and radially displace the dilator portions to allow one or more elongate medical devices to pass therebetween. Advantageously, the system maintains the elongate medical device in a sterile environment, mitigating the introduction of pathogens and the like.

Disclosed herein is a catheter placement system including, a catheter housing defining a longitudinal axis, an elongate medical device disposed within an interior cavity of the catheter housing, and a needle housing including a needle extending distally therefrom, the needle housing releasably coupled to a distal end of the catheter housing and including a needle retraction mechanism configured to split the needle along a longitudinal axis and retract the needle into the needle housing.

In some embodiments, the needle housing includes a needle retraction lever hingedly coupled thereto and configured to actuate a gear mechanism disposed within the needle retraction mechanism. In some embodiments, the needle retraction mechanism is configured to roll up a portion of the needle about an axis extending perpendicular to the longitudinal axis. In some embodiments, the needle includes a sheath disposed on an outer surface thereof, one of the needle or the sheath includes a breach line. In some embodiments, the elongate medical device includes one of a dilator, a catheter, or a guidewire. In some embodiments, one of the dilator or the catheter includes one of a polyether ether ketone (PEEK) material, or a fluorinated ethylene propylene (FEP) material. In some embodiments, the catheter housing includes a flexible section configured to elastically deform along an axis extending perpendicular to the longitudinal axis.

In some embodiments, the catheter housing includes an aperture extending through a side wall of the catheter housing and including a flexible film barrier disposed thereover. In some embodiments, the catheter housing includes a pleated section transitionable along the longitudinal axis between an extended configuration and a collapsed configuration. In some embodiments, the catheter housing is configured to rotate about the longitudinal axis to detach from the needle housing and split the needle housing along a longitudinal axis. In some embodiments, the catheter placement system further includes a dilator wedge splitter disposed within the catheter housing and configured split the dilator along the longitudinal axis. In some embodiments, the catheter housing includes a blood flash indicator releasably coupled to a proximal end thereof. In some embodiments, the catheter housing includes a guidewire housing extending from a proximal end thereof and configured to receive a portion of the guidewire therein. In some embodiments, a portion of one of the housing or the guidewire housing includes transparent material.

Also disclosed is a method of placing a catheter including, providing a catheter placement system having, a catheter housing including a flexible section and a pleated section, an elongate medical device, a portion thereof disposed within the catheter housing, and a needle housing releasably coupled to a distal end of the catheter housing and including a needle extending therefrom, accessing a vasculature of a patient, deforming the flexible section to grasp the portion of the elongate medical device disposed therebelow, transitioning the pleated section between an extended configuration and a collapsed configuration, releasing the flexible section to release the portion of the elongate medical device, and transitioning the pleated section between a configuration and an extended configuration.

In some embodiments, the elongate medical device includes one of a dilator, a catheter, or a guidewire. In some embodiments, the method further includes compressing a blood flash indicator to draw a fluid flow through the needle and confirm vascular access. In some embodiments the method further includes deforming a distal flexible section to grasp a first portion of the elongate medical device, transitioning the pleated section from the extended configuration to the collapsed configuration, deforming a proximal flexible section to grasp a second portion of the elongate medical device, releasing the first flexible section, and transitioning the pleated section from the collapsed configuration to the extended configuration to withdraw the elongate medical device proximally.

In some embodiments, the method further includes withdrawing the elongate medical device proximally, over a splitter disposed within the housing to split the elongate medical device along a longitudinal axis. In some embodiments the method further includes actuating a needle retraction mechanism to retract the needle into the needle housing. In some embodiments, actuating the needle retraction mechanism includes rotating a needle retraction lever that is hingedly coupled to the needle housing, the needle retraction lever actuating a gear mechanism within the needle retraction mechanism. In some embodiments, retracting the needle into the needle housing includes splitting the needle along a longitudinal axis and rolling up the needle about an axis extending perpendicular to the longitudinal axis. In some embodiments, the method further includes rotating the catheter housing to detach the catheter housing from the needle housing. In some embodiments, detaching the catheter housing from the needle housing includes splitting the needle housing along a longitudinal axis to separate a first portion of the needle housing from a second portion of the needle housing. In some embodiments, the method further includes attaching a connector set to a hub of the catheter. In some embodiments, coupling the connector set to the catheter hub includes one of an interference fit, a push fit, a snap fit, a threaded engagement, or a bayonet fitting.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 3A-3C illustrate cross-sectional side views of a catheter placement system, in accordance with embodiments disclosed herein.

FIG. 5C illustrates a cross-sectional view of a needle and sheath of a catheter placement system, in accordance with embodiments disclosed herein.

FIG. 5D illustrates a perspective view of a needle being rolled up, in accordance with embodiments disclosed herein.

FIG. 5E illustrates a cross-sectional view of a needle and sheath of a catheter placement system, in accordance with embodiments disclosed herein.

FIG. 5F illustrates a perspective view of a needle being rolled up, in accordance with embodiments disclosed herein.

DESCRIPTION

Figure 1:
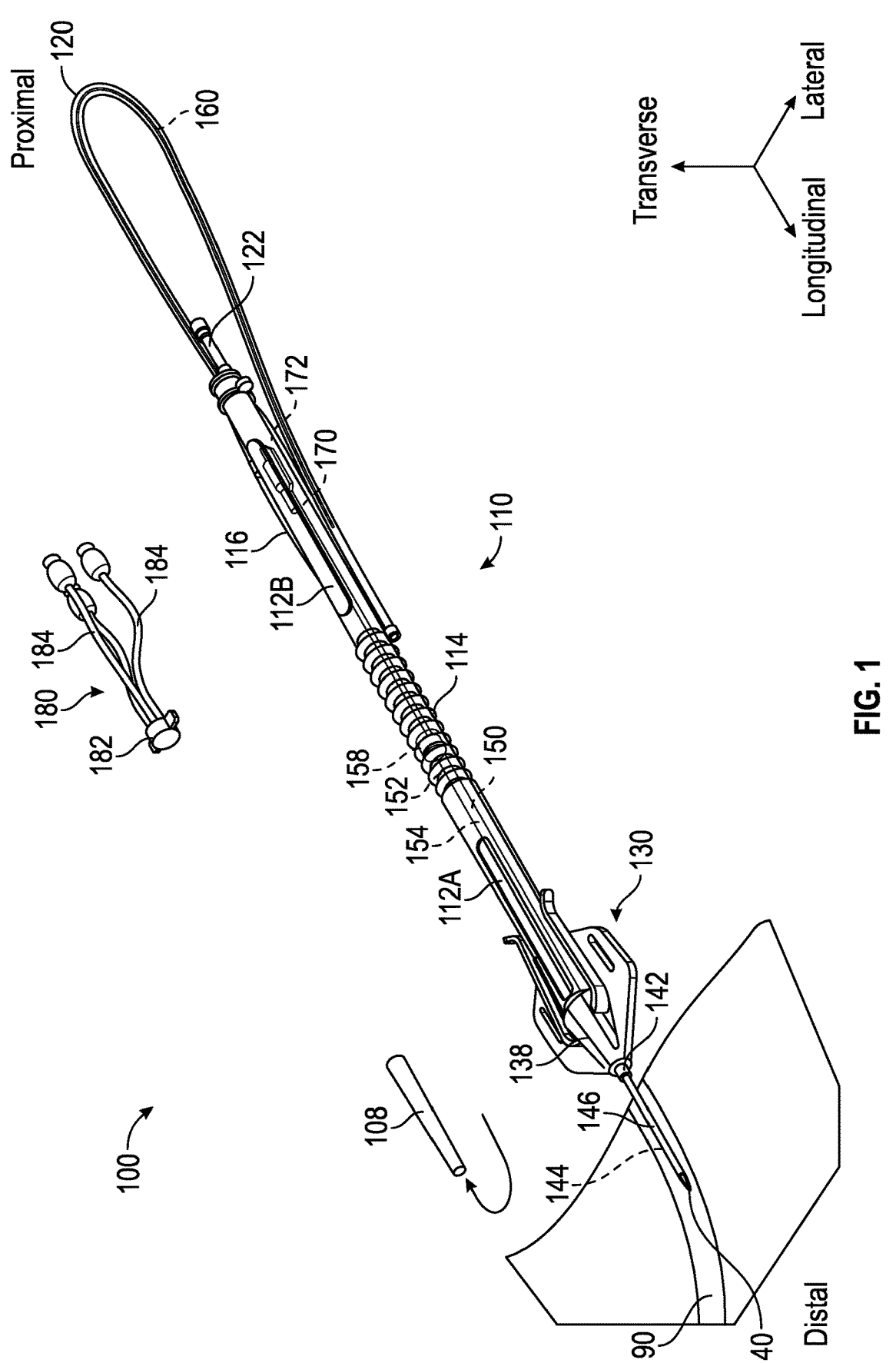
FIG. 1 illustrates a perspective view of a catheter placement system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle; however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle; however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

As shown in FIG. 1, and to assist in the description of embodiments described herein, a longitudinal axis extends substantially parallel to an axial length of a needle 140. A lateral axis extends normal to the longitudinal axis, and a transverse axis extends normal to both the longitudinal and lateral axes. A horizontal plane is defined by the longitudinal and lateral axes. A vertical plane can extend normal to the horizontal plane.

Unless defined otherwise, all technical and scientific terms used herein have the same meaning as commonly understood by those of ordinary skill in the art.

The present disclosure relates generally to a catheter placement system 100 including a splittable needle and dilator, and associated methods thereof. As used herein, a catheter placement system 100 can be used to place a central venous catheter (CVC) to access a vasculature of a patient. However, it will be appreciated that embodiments disclosed herein can be used to place various catheters, cannulas, single lumen catheters, multi-lumen catheters, intravenous (IV) catheters, peripherally inserted central catheters (PICC), Rapid Insertion Central Catheter (RICC), dialysis catheters, drainage catheters, and the like, without limitation.

FIG. 1 shows an exemplary embodiment of a catheter placement system ("system") 100 that generally includes a catheter housing 110 and a splittable needle housing 130, releasably coupled to a distal end of the catheter housing 110. The system 100 further includes a needle 140, a dilator 150, a guidewire 160, and a catheter 170. The catheter housing 110 defines a substantially elongate, cylindrical shape including a circular cross-sectional shape. However, it will be appreciated that other elongate and cross-sectional shapes including triangular, square, hexagonal, polygonal, or combinations thereof, are also contemplated. In an embodiment, a portion of the catheter housing 110 can define a polygonal cross-sectional shape to provide a gripping surface and facilitate rotation of a catheter housing 110.

In an embodiment, the catheter housing 110 can be formed of a rigid or semi-rigid material including metal, alloy, polymer, plastic, thermoplastic, elastomer, rubber, silicone rubber, combinations thereof, or the like. In an embodiment, an outer surface of the catheter housing 110 includes a compliant material, elastomer, or the like, to provide a comfortable gripping surface and facilitate manipulation of the system 100. In an embodiment, the catheter housing 110 can be formed of a translucent or transparent material to allow a user to observe structures, components, or elongate medical devices, disposed therein.

In an embodiment, the catheter housing 110 can include a barrier 116 extending over an outer surface thereof. The barrier 116 can extend from the needle housing 130, disposed at a distal end, to a proximal end of the catheter housing 110, and extend annularly about a longitudinal axis of the catheter housing 110. In an embodiment, the barrier 116 can be formed of a thin polymer film or similar flexible material configured to allow a user to manipulate one of the catheter housing 110, or an elongate medical device disposed therein. As used herein, an "elongate medical device" can include one or more of the needle 140, dilator 150, catheter 170, guidewire 160, or one or more advancement assemblies configured to manipulate one of the needle 140, dilator 150, catheter 170, guidewire 160, combinations thereof, or the like. In an embodiment, the barrier 116, or portion thereof, can be transparent to allow a user to observe one of the catheter housing 110, or an elongate medical device, disposed therein.

Figure 2A:
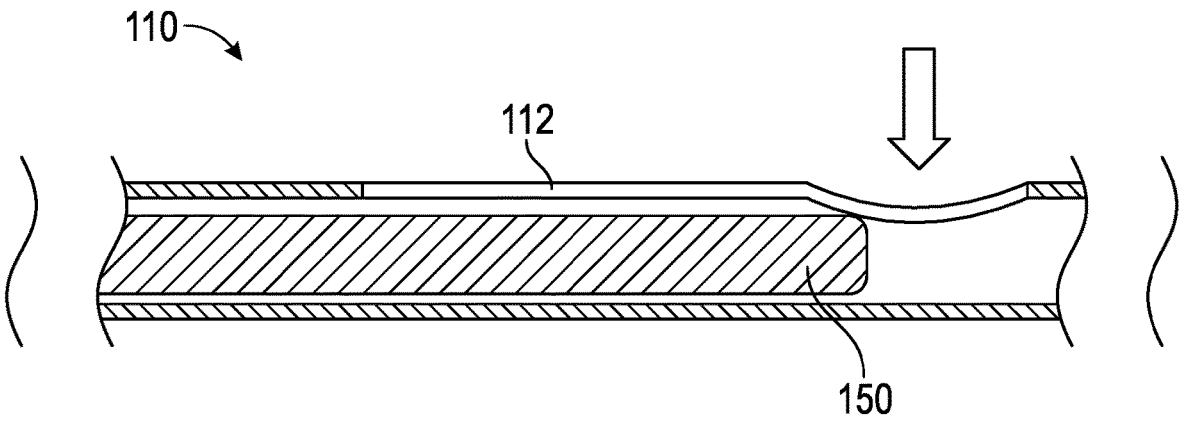
FIGS. 2A-2B illustrate cross-sectional side views of a catheter placement system, in accordance with embodiments disclosed herein.

In an embodiment, the catheter housing 110 can include one or more flexible sections 112, for example a distal flexible section 112A and a proximal flexible section 112B. As used herein a "flexible section" can include a portion of the catheter housing that can be elastically deformed along an axis that is perpendicular to a longitudinal axis of the system 100. The flexible section 112 can include a portion of the wall of the catheter housing 110 that defines more flexible mechanical properties. In an embodiment, as shown in FIG. 2A, a flexible section 112 can include a portion of a side wall of the catheter housing 110, e.g., a top side wall. In an embodiment, the flexible section 112 can include a first portion of a side wall and a second portion of the side wall, disposed opposite the first portion across a central longitudinal axis 80, e.g. laterally where the flexible section includes a left portion and a right portion, transversely where the flexible section includes a top portion and a bottom portion, or combinations thereof. In an embodiment the flexible section 112 can include a portion of the side wall that extends annularly about the longitudinal axis.

In an embodiment, the flexible section 112 can include a different material from that of the catheter housing 110. In an embodiment, the flexible section 112 can define a different wall thickness of material from that of the catheter housing 110. In an embodiment, a user can elastically deform the flexible section 112 to grasp or manipulate an elongate medical device or advancement assembly disposed within the catheter housing 110.

For example, as shown in FIG. 2A, a user can deform a portion of the flexible section 112 to constrict the interior cavity of the catheter housing 110 disposed therebelow. The constricted portion can be distally or proximally of an end of an elongate medical device (e.g. dilator 150) or an advancement assembly coupled to an elongate medical device, disposed within the catheter housing 110. The deformed portion can constrict the interior diameter of the catheter housing 110 to a diameter that is less than an outer diameter of the elongate medical device 150.

Figure 2B:
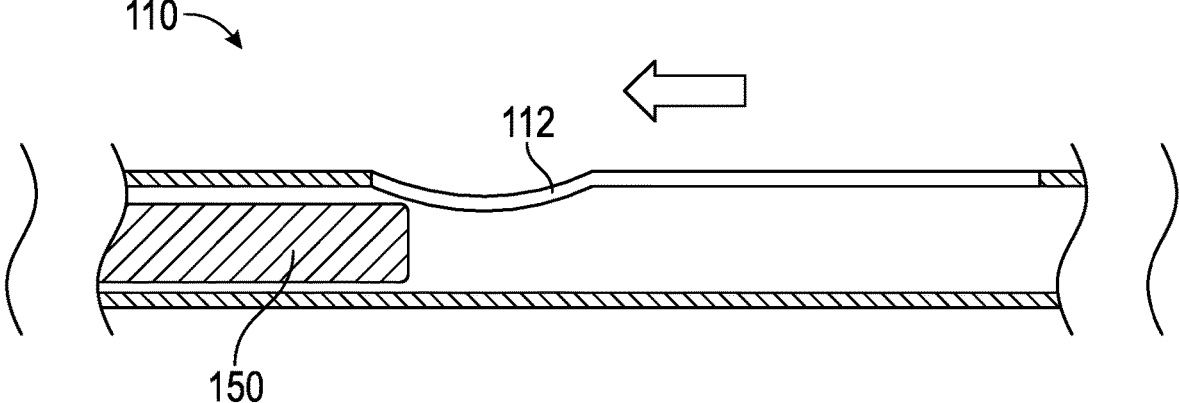

As shown in FIG. 2B, the user can then slide the deformed portion along a longitudinal axis of the flexible section 112 in a "wave-like" action. Worded differently, a user can constrict adjacent portions of the flexible section 112 along a longitudinal axis of the flexible section 112. As such, the elongate medical device 150 can be urged through the interior cavity of the catheter housing 110 in front of the deformed portion.

In an embodiment the flexible section 112 can include more transparent properties relative to the catheter housing 110 to allow a user to observe an elongate medical device disposed therebelow. Advantageously, a user can manipulate the elongate medical device, disposed within the catheter housing 110 without having to directly contact the elongate medical device. This maintains the elongate medical device in a sealed environment and mitigates the introduction of pathogens, or similar infection causing agents.

In an embodiment, the flexible section 112 can include an aperture extending through a side wall of the catheter housing 110. For example, as shown in FIGS. 3A-3C, in an embodiment, the aperture flexible section 112 can include a flexible barrier 116 disposed thereover to maintain a sterile environment. As shown in FIG. 3B, a user can compress a portion of the barrier 116 through one or more flexible section apertures 112 to grasp an elongate medical device, (e.g. dilator 150), disposed within the catheter housing 110. As shown in FIG. 3C, a user can then slide the grasped portion longitudinally to advance proximally, or withdraw distally, the elongate medical device though the catheter housing 110. Advantageously, the aperture flexible section 112 together with the barrier 116 disposed thereover can allow a user to manipulate an elongate medical device disposed within the catheter housing 110 while maintaining a sterile barrier therebetween.

In an embodiment, the catheter housing 110 can include a pleated section 114. As used herein a "pleated section" includes a portion of the catheter housing 110 that can be expanded or collapsed along a longitudinal axis. In an embodiment, the pleated section 114 can include one or more folded pleats configured to allow the catheter housing 110 to transition between an extended configuration and a collapsed configuration, extending or collapsing along a longitudinal axis. However, it will be appreciated that other configurations of the catheter housing 110 configured to extend or collapse along a longitudinal axis, such as a telescoping section, sliding section, folding section, combinations thereof, or the like, are also contemplated to fall within the scope of the present invention.

Figure 4A:
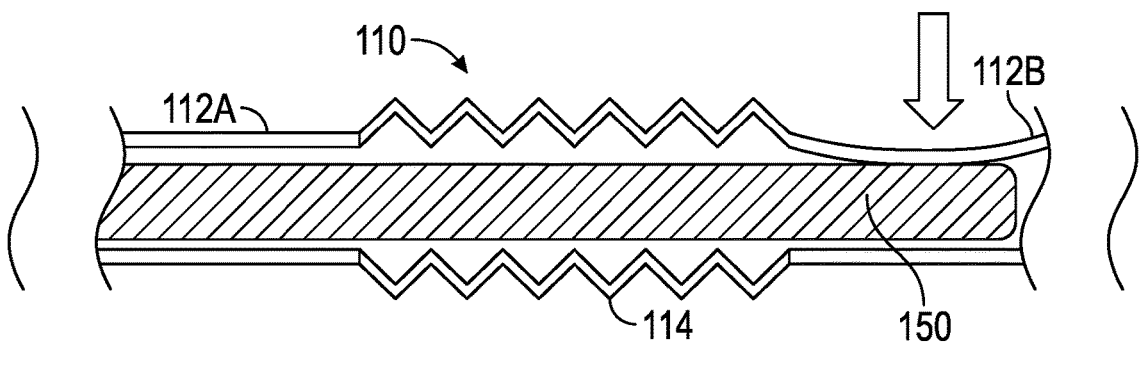
FIGS. 4A-4C illustrate cross-sectional side views of a catheter placement system, in accordance with embodiments disclosed herein.
Figure 4B:
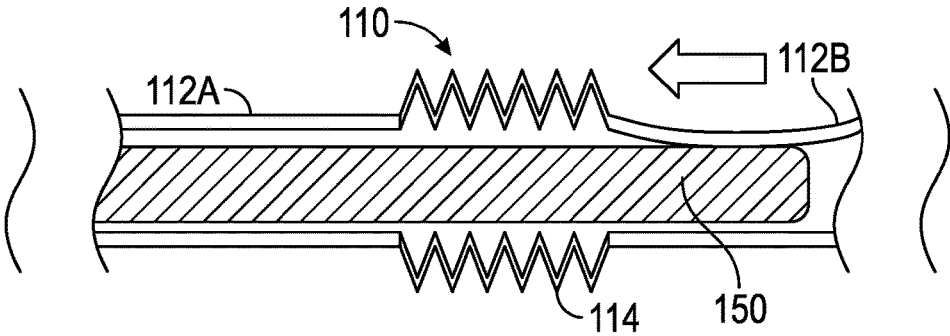
Figure 4C:
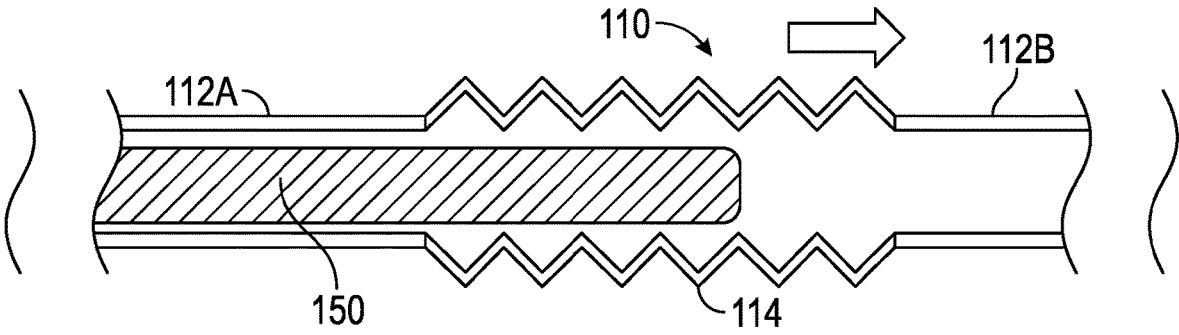

FIGS. 4A-4C show a cross-sectional view of the catheter housing 110 including a distal flexible section 112A, a proximal flexible section 112B, a pleated section 114, and an elongate medical device, e.g. a dilator 150, disposed within the catheter housing 110. In an exemplary method of use, a user can compress a proximal flexible section 112B to grasp a portion of the dilator 150 disposed therein. The user can transition the pleated section 114 from the extended configuration (FIG. 4A) to the collapsed configuration (FIG. 4B). As such, the dilator 150 grasped within the housing 110, can be advanced distally. The user can then release the proximal flexible section 112B and transition the pleated section 114 from the collapsed configuration (FIG. 4B) to the extended configuration (FIG. 4C). Optionally, a user can compress the distal flexible section 112A to grasp the dilator 150 in the distal position as the pleated section 114 transitions from the collapsed configuration to the extended configuration to prevent retrograde movement of the dilator 150 during the transition. As will be appreciated, a user can repeat the process as necessary to continue to advance the dilator 150 in a proximal direction.

In like manner, to withdraw the elongate medical device proximally, a user can compress a distal flexible section 112A to grasp a portion of the dilator 150 disposed therein. The user can then transition the pleated section 114 from the extended configuration to the collapsed configuration. A user can release the portion of the dilator 150 disposed adjacent the distal flexible section 112A and deform the proximal flexible section 112B to grasp a second portion of the dilator 150. The user can then transition the pleated section 114 from the collapsed configuration to the extended configuration to withdraw the dilator 150 proximally. A user can repeat the process as necessary to continue to withdraw the dilator 150 in a proximal direction. As will be appreciated, the dilator 150 is an exemplary elongate medical device and that the dilator 150, guidewire 160, catheter 170, combinations thereof, or the like can be advanced distally, or withdrawn proximally, as described herein. As will be appreciated, while a compressible flexible section 112 is shown, one or more aperture flexible sections 112 (e.g. FIGS. 3A-3C) can be also be used in place of one or more compressible flexible sections 112 and still fall within the scope of the present invention.

With continued reference to FIG. 1, the system 100 can include a needle 140, supported by a needle hub 142, coupled to a distal end of the needle housing 130. The needle 140 can define a needle lumen 144 and, in an embodiment, include a needle sheath 146 disposed on an outer surface thereof. In an embodiment, the sheath 146 can be a peripherally inserted venous (PIV) catheter that can define a smaller outer diameter than the catheter 170. The sheath 146 can maintain access to the insertion site as one or more of the needle 140, dilator 150, guidewire 160 or catheter 170 are exchanged. In an embodiment, the sheath 146 can be configured to support a first half and a second half of a needle 140 to define a needle lumen 140, as described in more detail herein. In an embodiment, the sheath 146 can be formed of a plastic, polymer, elastomer, urethane, or similar suitable material.

In an embodiment, the system 100 can further include a dilator 150 disposed within the catheter housing 110. The dilator 150 can be supported by a dilator hub 152 and define a dilator lumen 154. In an embodiment, the dilator 150 can include a plastic, polymer, polyether ether ketone (PEEK) material, or a fluorinated ethylene propylene (FEP) material, or similar suitable material. In an embodiment, the dilator 150 can be supported by a dilator advancement assembly (not shown) configured to facilitate manipulation of the dilator 150 within the catheter housing 110 by way of one of the flexible sections 112, or pleated section 114, as described herein.

In an embodiment, a catheter 170 can be disposed within the catheter housing 110 and can be supported by a catheter hub 172. The catheter 170 can be configured to fit through the dilator lumen 154. The catheter hub 172 can be configured to be manipulated by a user, through one or more of the flexible sections 112 to advance or withdraw the catheter 170, as described herein. In an embodiment, the catheter 170 can be supported by a catheter advancement assembly (not shown) configured to facilitate manipulation of the catheter 170 within the catheter housing 110 by way of one of the flexible sections 112, or pleated section 114, as described herein. In an embodiment, the catheter 170 can include a plastic, polymer, polyether ether ketone (PEEK) material, or a fluorinated ethylene propylene (FEP) material, or similar suitable material.

In an embodiment, a guidewire housing 120 can extend from a proximal end of the catheter housing 110 and define an interior cavity that communicates with an interior cavity of the catheter housing 110. The guidewire housing 120 can be configured to receive a portion of the guidewire 160 disposed therein. In an embodiment, the guidewire housing 120 can be formed of a flexible material and can allow a user to manipulate the guidewire 170 disposed therein. In an embodiment, the guidewire housing 120 is formed of flexible plastic, polymer, elastomer, or the like. A user can compress a portion of the guidewire housing 120 disposed proximally of the proximal end of the guidewire 160 to occlude the interior cavity of the guidewire housing 120. The user can then slide the occluded portion of the guidewire housing 120 distally in a "wave-like" manner, as described herein, to urge the guidewire 160 distally, ahead of the occluded portion.

In an embodiment, the guidewire housing 120 is formed of a thin film or similar collapsible barrier. A user can grasp the guidewire 160 by compressing an outer portion of the guidewire housing 120. The user can then urge the guidewire 160 distally into the catheter housing 110. The portion of guidewire housing 120 disposed distally of the grasped portion of guidewire 160 can collapse to allow distal advancement of the guidewire 160. In an embodiment, the guidewire housing 120 can be formed of a transparent material to allow a user to observe a portion of the guidewire 170 disposed therein. In an embodiment, the guidewire 170 can extend from the guidewire housing 120 through one of the catheter 170, dilator 150, needle 140, or portion thereof, disposed within the catheter housing 110.

In an embodiment, the system 100 can further include a blood flash indicator 122. The blood flash indicator 122 can include a tube or similar structure formed from a flexible, transparent material and can extend from a proximal end of the catheter body 110. The blood flash indicator 122 can define an interior cavity. In an embodiment, the interior cavity can be configured to maintain a vacuum therein. The blood flash indicator 122 can be in fluid communication with a lumen of the needle 140 by way of a communicating tube 124. As a distal tip of the needle 140 accesses a vasculature of the patient, a fluid (e.g. blood) can flow proximally into the blood flash indicator 122 to be observed by a user. In an embodiment, a vacuum disposed within the blood flash indicator 122 can draw a fluid (e.g. blood) proximally through the communicating tube 124 and into the blood flash indicator 122. A user can then observe a color or pulsatile flow characteristics to confirm correct vascular access.

In an embodiment, the system 100 further includes a cap 108 configured to releasably engage with a distal end of one of the catheter housing 110 or the needle housing 130, and cover a distal portion of one or more of the needle 140, needle sheath 146, or the dilator 150. The cap 108 can mitigate accidental needle stick injuries during storage or transport and maintains the needle 140, needle sheath 146, the dilator 150 etc. in a sterile environment. The system 100 can further include a connector set 180 configured to engage a proximal end of the catheter 170. The connector set 180 can include a connector hub 182 and one or more extension legs 184 configured to provide fluid communication with one or more lumen of the catheter 170.

FIGS. 5A-5D show further details of the needle 140 and the splittable needle housing 130. The needle housing 130 can include a coupling 132 configured to releasably couple the needle housing 130 to the catheter housing 110. The needle housing 130 can further include one or more stabilization wings ("wings") 134, e.g. a right stabilization wing 134A and a left stabilization wing 134B. The wing(s) 134 can extend laterally from the needle housing 130 and define an extended lower surface configured to engage a skin surface of the patient and mitigate rotational movement about the longitudinal axis. Optionally, the wing(s) 134 can include one or more apertures configured to engage a strap, tape, dressing, bandage, or similar securement device to facilitate securing the needle housing 130 to a skin surface of the patient. In an embodiment, a surface of the needle housing 130 can include an adhesive layer disposed thereon and configured to secure the needle housing 130 to a skin surface of the patient. Optionally the strap, tape, dressing, bandage, adhesive layer or the like can provide a sterile barrier between catheter placement system 100 and the insertion site.

The needle housing 130 can further include a needle retraction mechanism 190. The needle retraction mechanism 190 can include one or more levers, gear mechanisms, ratchet mechanisms, sector gears, over-run slip clutches, or the like, configured to couple with the needle hub 142 and retract the needle 140 proximally into one of the needle housing 130 or the catheter housing 110 leaving the sheath 146 within the insertion site to maintain patency of the insertion site. In an embodiment, the guidewire 160 can be advanced through the needle lumen 144 to maintain patency of the insertion site and one or both of the needle 140 and the sheath 146 can be retracted into the needle housing 130, as described herein.

In an embodiment, the needle retraction mechanism 190 can be configured to split the needle 140 along a longitudinal axis and roll up the needle 140 on itself. The needle 140 can then be stored within the needle housing 130. Splitting and storing the needle 140 in this manner displaces the needle radially outward from a central longitudinal axis 80, and provides a clear channel for one or more elongate medical devices to advance distally therebetween.

As shown in FIGS. 5C-5F, in an embodiment, one of the needle 140 or the sheath 146 can include a breach line 148 extending longitudinally. As used herein, a "breach line" can include a laser cut line, perforation, groove, score line, or the like configured to facilitate separation therealong. As shown in FIGS. 5C-5D, in an embodiment, the needle 140 can include a single breach line 148 extending longitudinally through one side of the needle 140. The needle 140 can be split along this breach line 148 to form a first side edge 148A and a second side edge 148B. The cylindrical shape of the needle 140 extending longitudinally can then be transitioned to a planar shape extending along an axis from the first side edge 148A to the second side edge 148A. The needle 140 can then be rolled up on itself along an axis extending perpendicular to the longitudinal axis and sequestered within the needle housing 130.

In an embodiment, the needle retraction mechanism 190 can be configured to split the needle 140 along two breach lines 148 to separate the needle 140 in to a first portion 140A and a second portion 140B. In an embodiment, as shown in FIG. 5E, the needle 140 can be formed as two separate portions 140A, 140B extending longitudinally that co-operate to form a needle lumen 144 and are held in place by the needle sheath 146. The needle retraction mechanism 190 then breaches the needle sheath 146 to separate the needle portions 140A, 140B. As shown in FIG. 5F, each of the needle portions 140A, 140B can be then transitioned from a semi-cylindrical shape to a planar shape before being rolled up on itself along an axis that extends perpendicular to the longitudinal axis.

Figure 5A:
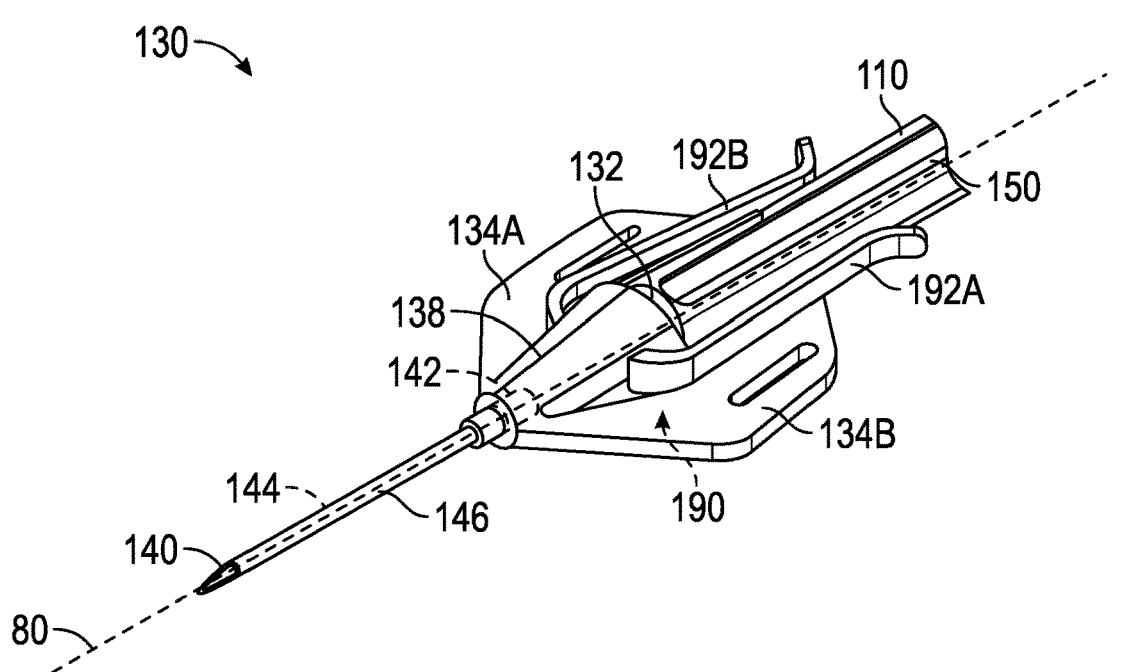
FIGS. 5A-5B illustrate perspective views of a needle housing of a catheter placement system, in accordance with embodiments disclosed herein.
Figure 5B:
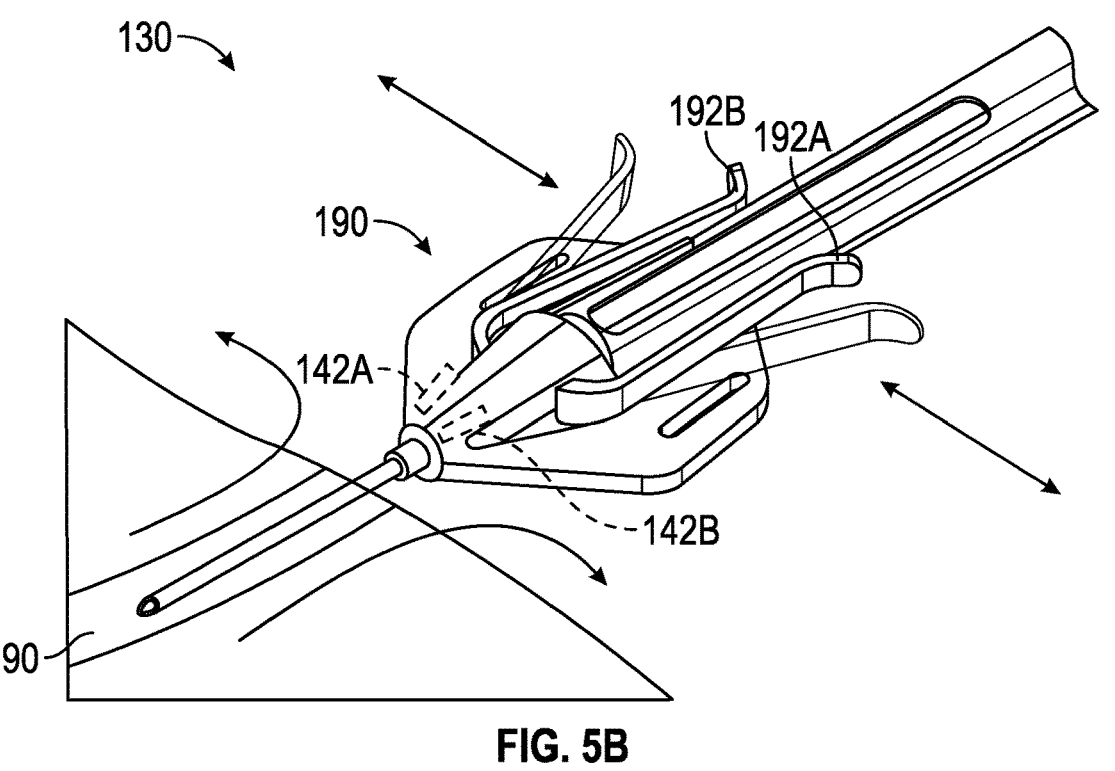

In an embodiment, as shown in FIG. 5B, the needle retraction mechanism 190 can include one or more levers 192 hingedly coupled to the needle housing 130 and configured to rotate through a horizontal plane. However, it will be appreciated that the one or more levers 192 may also rotate through a vertical plane, or along a plane extending at an angle therebetween. Rotating the one or more levers 192 can split the needle hub 142 into two separate portions 142A, 142B, and proximally retract the needle 140 into the needle housing 130. In an embodiment, a single rotation of the lever(s) 192 can split and fully retract the needle 140. In an embodiment, the needle retraction mechanism 190 can include a ratchet mechanism configured to allow one or more rotations of the lever(s) 192 to split and fully retract the needle 140. In an embodiment, the retraction mechanism 190 can link the first retraction lever 192A and the second retraction lever 192B such that actuating one of the first retraction lever 192A or the second retraction lever 192B causes both of the retraction levers 192A, 192B to rotate. In an embodiment, the needle retraction mechanism 190 can further include a biasing member to bias the levers towards a starting position, e.g. as shown in FIG. 5A. A user can then actuate the levers 192 from the starting position to an actuated position. Releasing the retraction levers 192 can then allow the biasing member to transition the retraction levers 192 from the actuated position to the starting position.

Figure 6A:
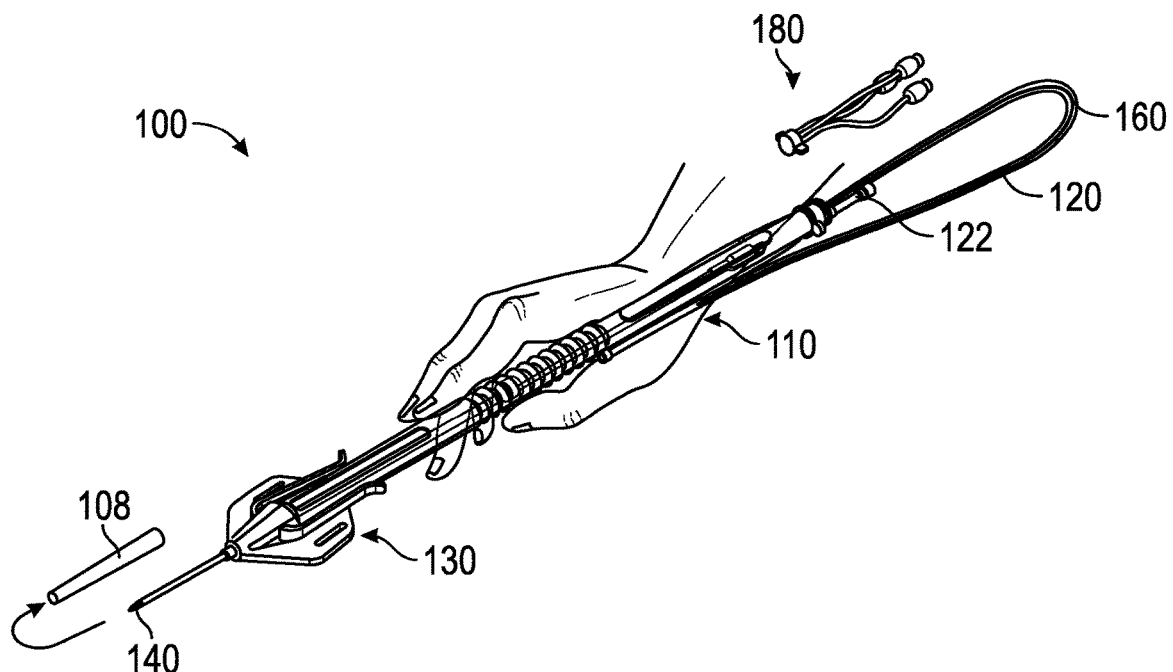
FIGS. 6A-6J illustrate various steps in an exemplary method of use of a catheter placement system, in accordance with embodiments disclosed herein.
Figure 6B:
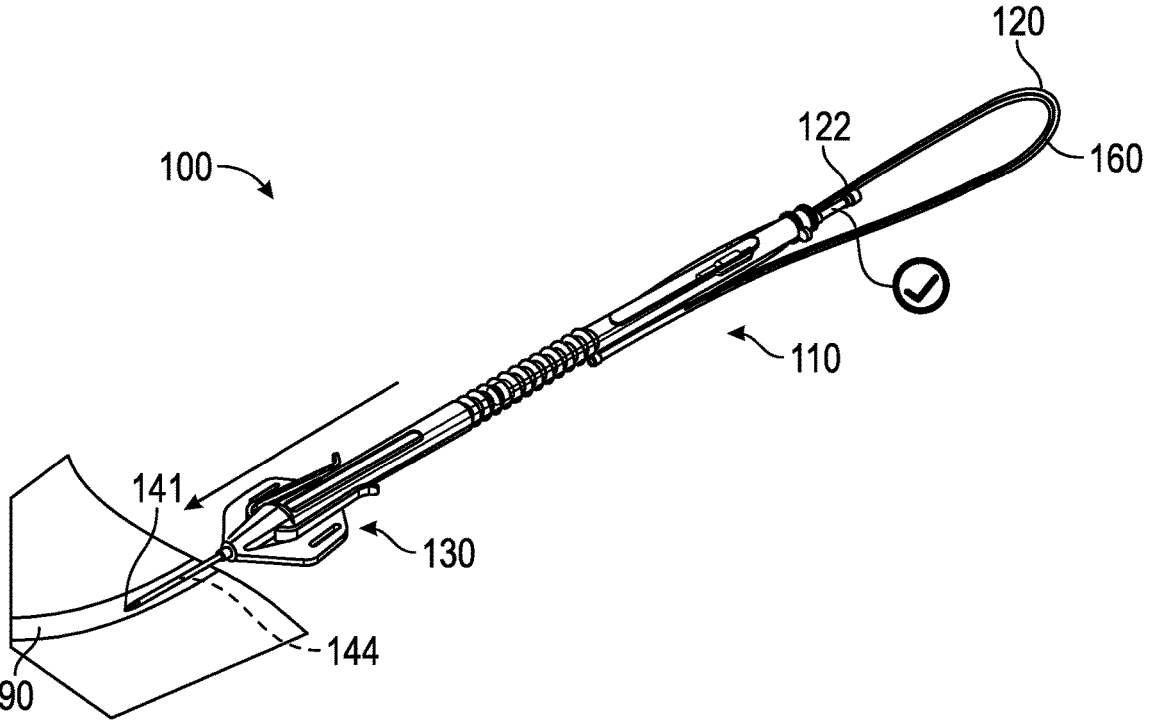

FIGS. 6A-6J show an exemplary method of use for a catheter placement system 100 as described herein. Initially, as shown in FIG. 6A, a user can flush the connector set 180 and cap off the ends of the connector set 180 and set to one side. The catheter placement system cap 108 can be removed from the needle housing 130 to expose the needle 140. As shown in FIGS. 6A-6B, a user can grasp the catheter housing 110 and urge the needle tip 141 into a vasculature 90 of a patient. It is important to note that the catheter placement system 100 provides all of the components for placing a catheter 170, i.e. needle 140, blood flash indicator 122, PIV sheath 146, dilator 150, guidewire 160, as well as the catheter 170 itself (e.g. a CVC catheter), contained within a single sterile unit. This maintains all components that may be exposed to the patient's vasculature 90 within a sterile environment and contrasts with existing procedures that require multiple components, which are exposed, and risk introducing infection at every stage. Further, the catheter placement system 100 maintains a barrier between the user and exposure to the patients' blood that also protects the user from potential exposure.

As shown in FIG. 6B, as the needle tip 141 accesses a vasculature 90 a blood flow can flow proximally through the needle lumen 144. In an embodiment, the vacuum disposed within the blood flash indicator 122 draws the blood flow through the communicating tube 124 and into the blood flash indicator 122. A user can then observe a color and pulsatile flow characteristics of the fluid disposed within the blood flash indicator 122 to confirm correct vascular access. For example a bright red color or strong pulsatile flow can indicate arterial access, a dark red color and low pulsatile flow can indicate venous access. Optionally, a user can compress the flexible blood flash indicator tube 122 to induce blood to flow therein.

Figure 6C:
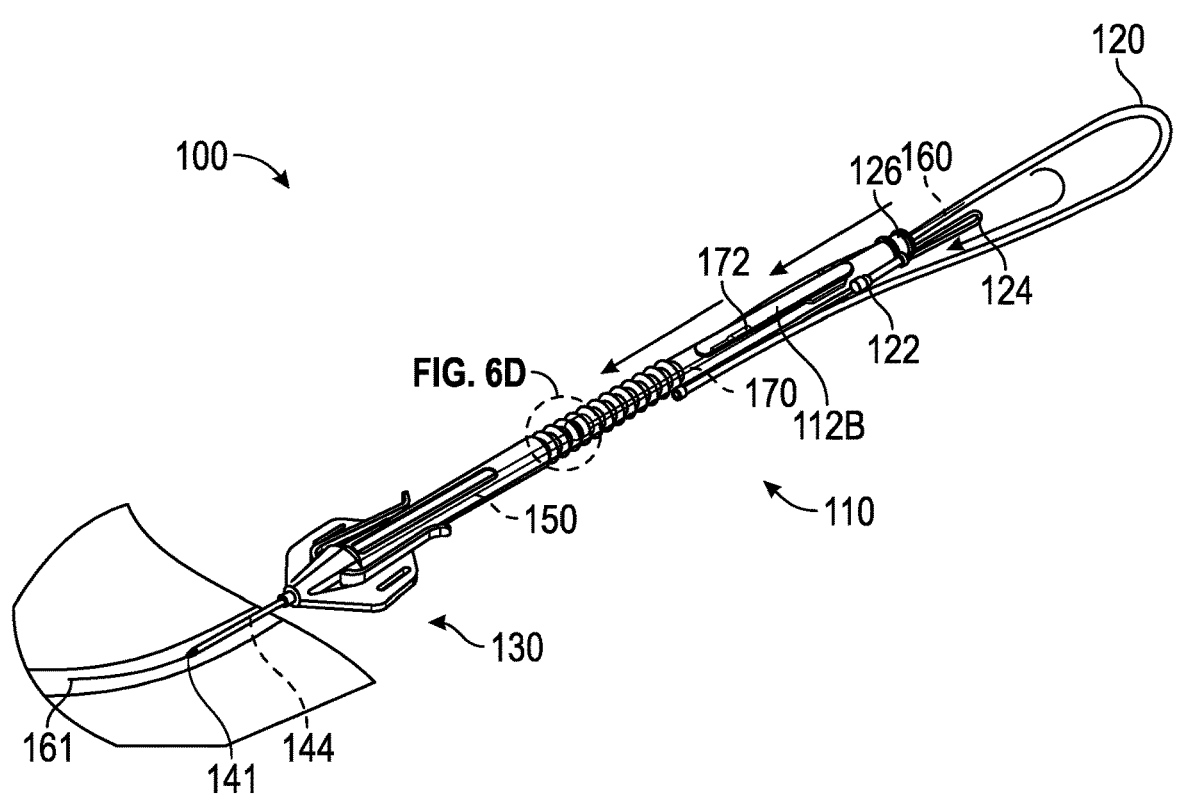

As shown in FIG. 6C, with the vascular access confirmed, the blood flash indicator 122 can be urged proximally to disengage the blood flash indicator 122 from the proximal end of the catheter housing 110. A portion of the communicating tube 124 is also withdrawn from the catheter housing 110 which in turn withdraws a distal end of the communicating tube 124, disengaging the communicating tube 124 from the needle lumen 144. The blood flash indicator 122 can then be removed and discarded, or secured to an outer surface of the catheter housing 110 using a clip or similar suitable means.

Figure 6D:
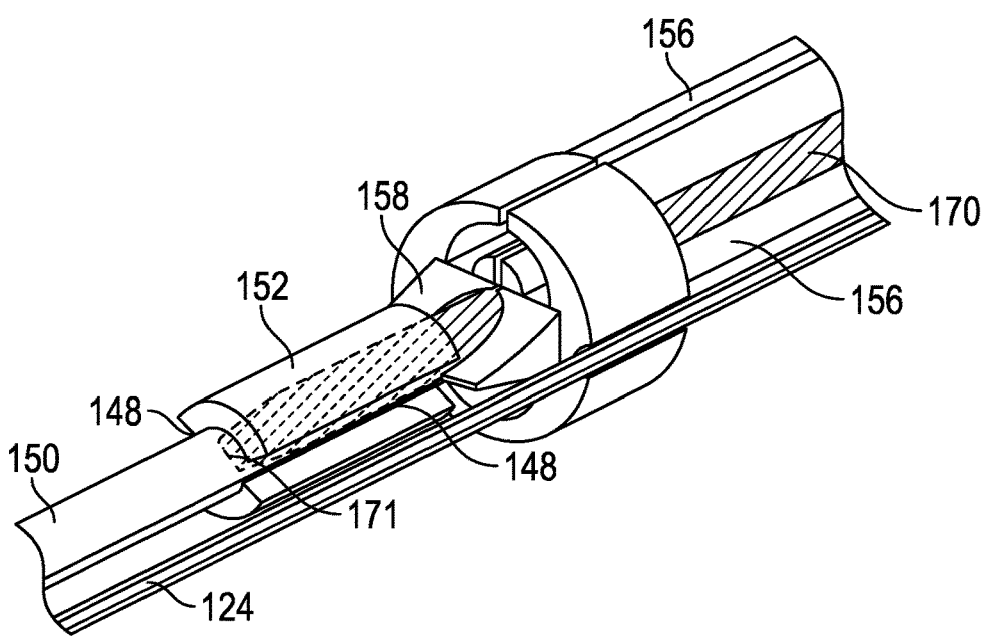

With the communicating tube 124 disengaged from the needle lumen 144, one of the catheter 170 or the dilator 150 can be advanced slightly so that a distal tip of the dilator 150 can engage a proximal end of the needle lumen 144. As shown in FIG. 6D, a distal tip 171 of the catheter 170 engages a proximal end of the dilator 150. As such the catheter 170, dilator 150 and needle 140 co-operate to provide a continuous path for the guidewire 160 to be advanced into the vasculature 90 of the patient.

In an embodiment, the catheter housing 110 includes a locking mechanism 126 configured to engaged the guidewire 160 extending therethrough and lock the guidewire 160 relative to the catheter housing 110. A user can unlock the guidewire 160, advance a portion of the guidewire 160 and then lock the guidewire 160 in position to prevent the guidewire being drawn into the vasculature 90 of the patient. In an embodiment, the guidewire 160 can advance through the catheter 170, through the dilator 150, through the needle 140 until a guidewire distal tip 161 advances distally of a needle distal tip 141. In an embodiment, the guidewire tip 161 can be advanced to a target location within the vasculature 90 of the patient. In an embodiment, the guidewire lock 126 can include either rotational locking mechanism or a push-button locking mechanism.

Figure 6E:
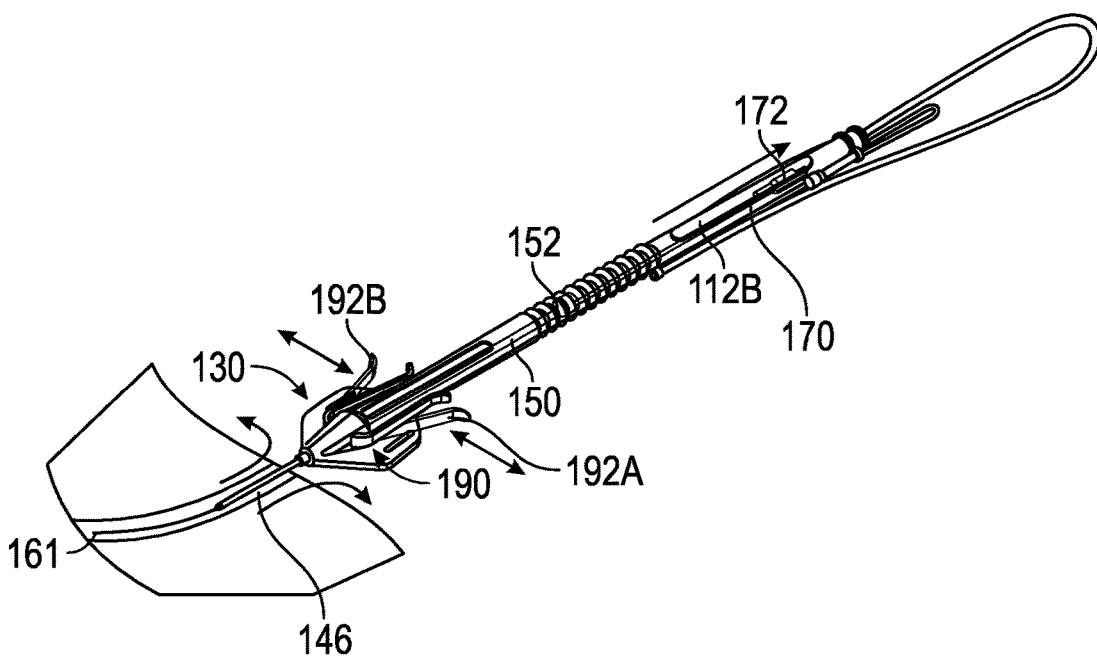

As shown in FIG. 6E, with the guidewire tip 161 advanced into the vasculature 90 of the patient, the needle 140 can be withdrawn out of the way to allow the dilator 150 to advance. In an embodiment, the dilator 150 and the catheter 170 can be withdrawn slightly to disengage a dilator tip 151 from the needle lumen 144. A user can then manipulate the needle retraction levers 192A, 192B, to retract the needle 140 proximally.

Actuating the needle retraction levers 192A, 192B can retract and split the needle hub 142 and the needle 140 into two separate portions, i.e., a first needle hub portion 142A, and a second needle hub portion 142B, and a first needle portion 140A, and a second needle portion 140B. Each portion 140A, 140B can then be rolled up on itself within the needle housing 130 to sequester the needle 140 away from the central longitudinal axis 80 to allow one or more elongate medical devices to pass axially therebetween. As described herein, the needle retraction mechanism 190 can include a biasing member, ratchet mechanism and the like to provide mechanical advantage and facilitate splitting and removal of the needle 140.

In an embodiment, the sheath 146 can be split and rolled up along with the needle 140. In an embodiment, the needle 140 is formed from two separate halves 140A, 140B, which are held together by the sheath 146. As such, removal of the needle 140 includes splitting the sheath 146 along a longitudinal axis and rolling up a first half of the sheath with a first half of the needle 140A, and a second half of the sheath with a second half of the needle 140B. In an embodiment, the needle is withdrawn, split and rolled up, and the sheath 146 is left in place within the insertion site to maintain patency of the vascular access site.

Figure 6F:
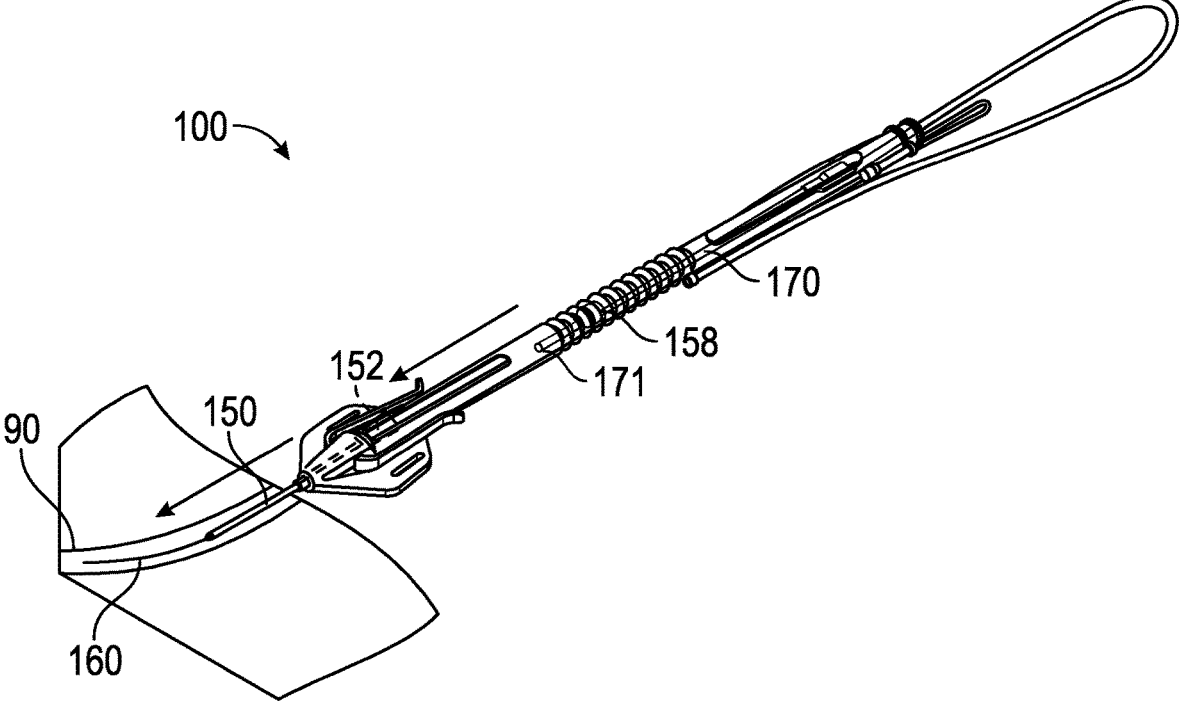

As shown in FIG. 6F, with the needle 140 withdrawn and sequestered into the needle housing 130, the dilator 150 can be advanced distally over the guidewire 160, and optionally over the sheath 146 into the vasculature 90 of the patient to dilate the vascular access site. The dilator 150 can be advanced by manipulating the dilator hub 152 through the flexible sections 112A, 112B and/or pleated section 114 as described herein. In an embodiment, the dilator hub 152 can be coupled to a distal end of a dilator advancement assembly (not shown) that extends proximally through the catheter housing 110. The user can then manipulate the dilator advancement assembly to advance or withdraw the dilator 150, through the flexible sections 112A, 112B and/or pleated section 114, as described herein.

Figure 6G:
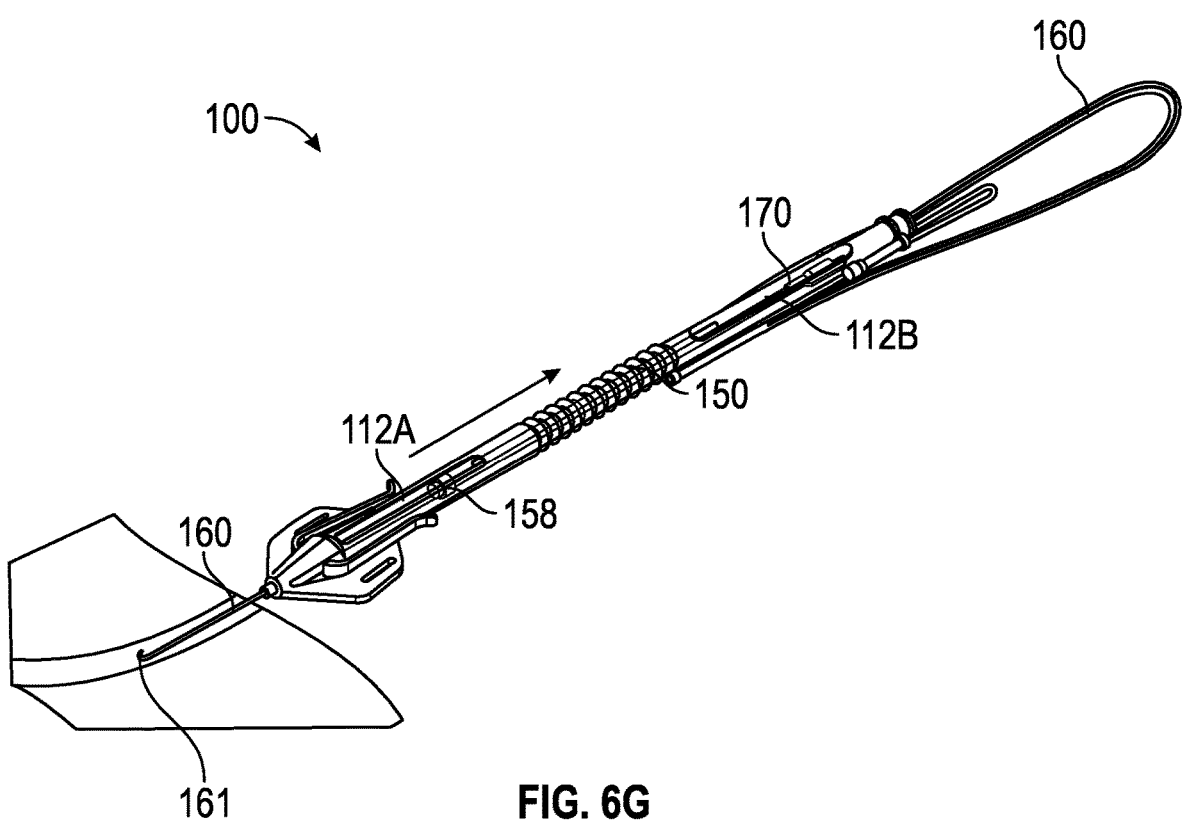

As shown in FIG. 6G, with the insertion site dilated, the dilator 150 can be withdrawn proximally either by manipulating the dilator hub 152 through the distal flexible section 112A, or by manipulating the dilator advancement assembly, as described herein. As the dilator 150 is being urged proximally into the catheter housing 110, the dilator 150 can be urged over a dilator splitter 158. As shown in FIG. 6D, the splitter 158 can include a wedge-shaped distal tip configured to split the dilator 150 along a longitudinal axis as the dilator 150 is urged proximally thereover. In an embodiment, the dilator 150 can further include a breach line 148 to facilitate separation of the dilator 150 into two halves. In an embodiment, the splitter 158 can be urged distally by manipulating a splitter arm 156 through the proximal flexible section 112B. The two dilator halves can be displaced radially outward relative to a central axis to allow one of the catheter 170 or guidewire 160 to pass longitudinally therebetween.

Figure 6H:
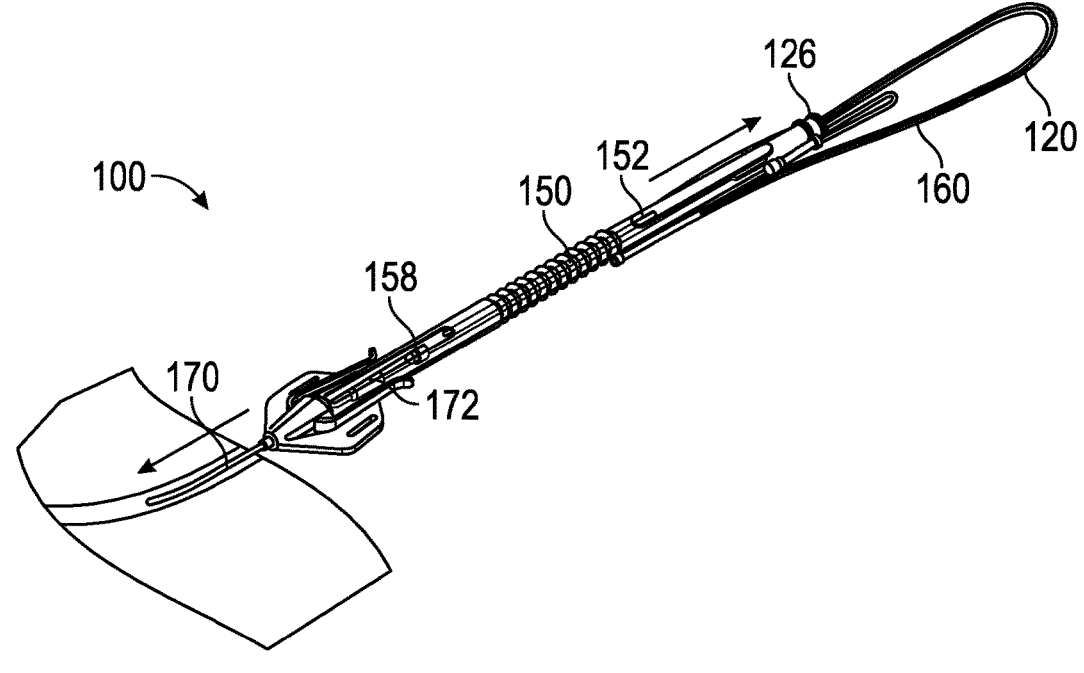

As shown in FIG. 6H, the catheter 170 can be advanced distally, over the guidewire 160 until a distal tip enters the vasculature 90 of the patient. The guidewire 170 can then be unlocked, using the guidewire lock 126, and withdrawn back into the catheter housing 110 and guidewire housing 120. When a distal tip of the guidewire 161 is disposed within the catheter housing 110, the guidewire 160 can then be locked into place using guidewire lock 126.

Figure 6I:
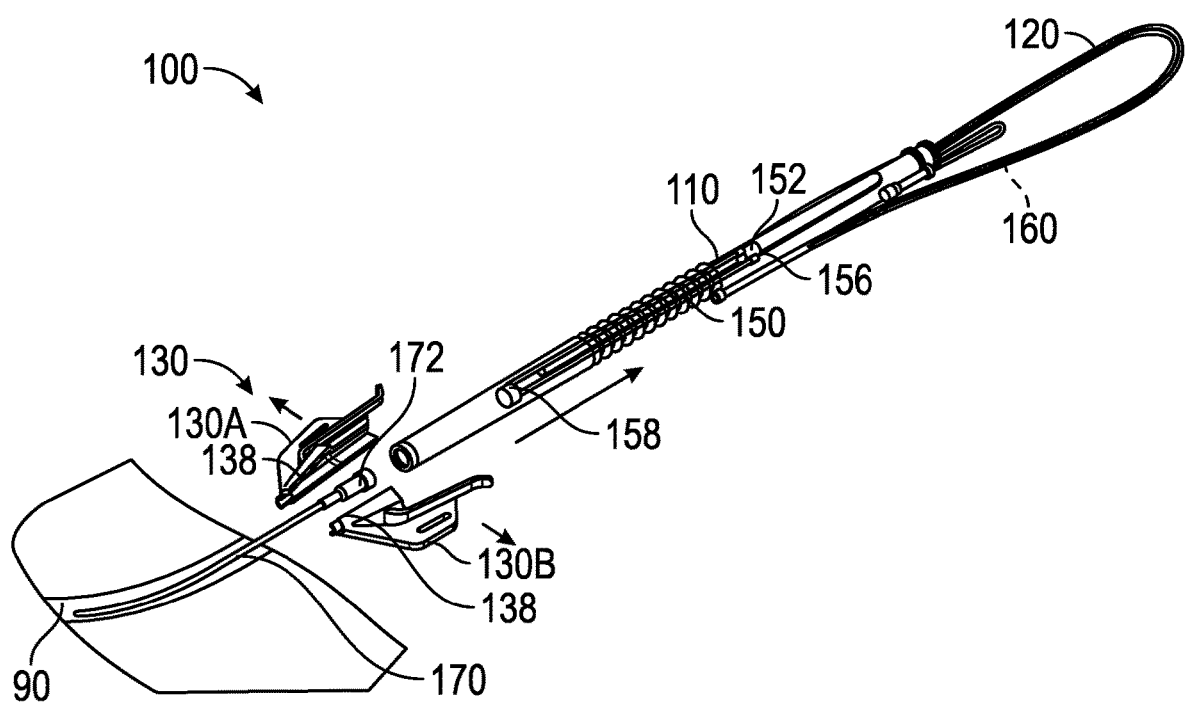

As shown in FIG. 6I, the catheter housing 110 with the dilator 150, splitter 158, and guidewire 160, disposed therein, can be detached from the needle housing 130 and discarded. In an embodiment, the catheter housing 110 can be detached by rotating the catheter housing 110 about the central longitudinal axis 80. With the catheter housing 110 detached from the needle housing 130, the needle housing 130 can be split along a longitudinal axis into two separate halves 130A, 130B. Each half 130A, 130B can then be separated perpendicular to the longitudinal axis to disengage the catheter hub 172. In an embodiment, the needle housing 130 can include a breach line 138 extending longitudinally and configured to facilitate separation of the needle housing first half 130A from the needle housing second half 130B. In an embodiment, the coupling 132 between the catheter housing 110 and the needle housing 130 can be configured to separate the needle housing 130 into two halves as the catheter housing 110 is rotated. For example, a distal end of the catheter housing 110 can include a cam lobe structure that engages needle housing 130 as the catheter housing 110 is rotated about the longitudinal axis. The cam lobe can provide a mechanical advantage to facilitate separation of the needle housing 130.

Figure 6J:
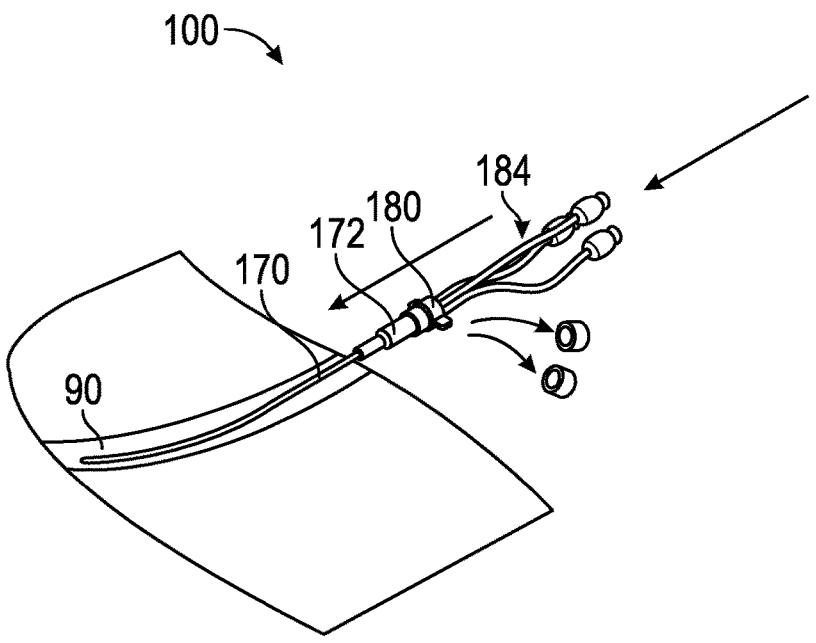

As shown in FIG. 6J, with the catheter housing 110 and needle housing 130 disengaged from the catheter 170, the connector set 180 can be coupled to the catheter hub 172. Each of the one or more extension legs 184 can fluidly communicate with a lumen of the catheter 170. In an embodiment, the connector set 180 can coupled to the catheter hub 172 with an interference fit, push fit, snap fit, threaded engagement, bayonet fitting, or the like.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter placement system for placing an elongate medical device into a vasculature of a patient, the catheter placement system comprising:
   a catheter housing in an assembled state defining a longitudinal axis;
   a catheter, disposed within an interior cavity of the catheter housing, the catheter housing encircling a portion of the catheter about the longitudinal axis; and
   a needle housing, a proximal end thereof releasably coupled to a distal end of the catheter housing to allow the needle housing to separate from the catheter housing, the needle housing comprising:
      a needle having a bevel tip where a bottom side of the needle extends to a distal-most tip, the needle extending distally from the needle housing and having a first breach line extending along a top side of the needle, the first breach line configured to allow the needle to separate therealong; and
      a needle retraction mechanism configured to retract the needle proximally into the needle housing prior to advancement of the catheter distally of the needle housing, the needle housing encircling a portion of one or both of the needle and the needle retraction mechanism about the longitudinal axis.

2. The catheter placement system according to claim 1, wherein the needle housing further includes a needle retraction lever hingedly coupled thereto and configured to actuate the needle retraction mechanism to retract the needle proximally.

3. The catheter placement system according to claim 1, wherein the needle retraction mechanism includes one or more levers, gear mechanisms, or ratchet mechanisms coupled to a needle hub of the needle and configured to retract the needle proximally into the needle housing by transitioning the needle to a planar shape and rolling the needle in the planar shape about an axis extending perpendicular to the longitudinal axis.

4. The catheter placement system according to claim 1, wherein the needle includes a sheath disposed on an outer surface thereof, and one of the needle or the sheath includes a breach line.

5. The catheter placement system according to claim 1, further including a dilator and a guidewire.

6. The catheter placement system according to claim 5, wherein one of the dilator or the catheter includes one of a polyether ether ketone (PEEK) material or a fluorinated ethylene propylene (FEP) material.

7. The catheter placement system according to claim 5, further including a dilator wedge splitter disposed within the catheter housing and configured to split the dilator along the longitudinal axis.

8. The catheter placement system according to claim 1, wherein the catheter housing includes a flexible section configured to elastically deform along an axis extending perpendicular to the longitudinal axis.

9. The catheter placement system according to claim 1, wherein the catheter housing includes an aperture extending through a side wall of the catheter housing and including a flexible film barrier disposed thereover.

10. The catheter placement system according to claim 1, wherein the catheter housing includes a pleated section transitionable along the longitudinal axis between an extended configuration and a collapsed configuration.

11. The catheter placement system according to claim 1, wherein the catheter housing is configured to rotate about the longitudinal axis to detach from the needle housing and split the needle housing along the longitudinal axis.

12. The catheter placement system according to claim 1, wherein the catheter housing includes a blood flash indicator releasably coupled to a proximal end thereof.

13. The catheter placement system according to claim 1, wherein the catheter housing includes a guidewire housing extending from a proximal end thereof and configured to receive a portion of a guidewire therein.

14. The catheter placement system according to claim 13, wherein a portion of one of the catheter housing or the guidewire housing includes a transparent material.

15. The catheter placement system according to claim 1, wherein the needle further includes a second breach line extending along the bottom side of the needle, opposite from the first breach line, the needle configured to separate along the first breach line and the second breach line into a first needle portion and a second needle portion.

* * * * *